(12) United States Patent
Dhar et al.

(10) Patent No.: US 9,725,443 B2
(45) Date of Patent: Aug. 8, 2017

(54) RORγ MODULATORS

(71) Applicant: BRISTOL-MYERS SQUIBB COMPANY, Princeton, NJ (US)

(72) Inventors: T. G. Murali Dhar, Newtown, PA (US); Jingwu Duan, Yardley, PA (US); Hua Gong, Newtown, PA (US); Bin Jiang, Bryn Mawr, PA (US); Zhonghui Lu, King of Prussia, PA (US); David S. Weinstein, East Windsor, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/022,673

(22) PCT Filed: Sep. 18, 2014

(86) PCT No.: PCT/US2014/056197
§ 371 (c)(1),
(2) Date: Mar. 17, 2016

(87) PCT Pub. No.: WO2015/042212
PCT Pub. Date: Mar. 26, 2015

(65) Prior Publication Data
US 2016/0229844 A1 Aug. 11, 2016

Related U.S. Application Data

(60) Provisional application No. 61/880,391, filed on Sep. 20, 2013.

(51) Int. Cl.
| A61K 31/47 | (2006.01) |
| C07D 417/06 | (2006.01) |
| C07D 401/06 | (2006.01) |
| C07D 401/12 | (2006.01) |
| C07D 413/14 | (2006.01) |
| C07D 215/58 | (2006.01) |
| C07D 413/06 | (2006.01) |

(52) U.S. Cl.
CPC ......... *C07D 417/06* (2013.01); *C07D 215/58* (2013.01); *C07D 401/06* (2013.01); *C07D 401/12* (2013.01); *C07D 413/06* (2013.01); *C07D 413/14* (2013.01)

(58) Field of Classification Search
CPC .... A61K 31/47; C07D 417/06; C07D 401/06; C07D 401/12; C07D 413/14; C07D 215/58; C07D 413/06
USPC ........ 514/211.09, 213.01, 221, 224.2, 230.5, 514/249, 312; 540/552, 573, 593; 544/52, 105, 353; 546/153
See application file for complete search history.

(56) References Cited

U.S. PATENT DOCUMENTS

2015/0191483 A1  7/2015  Duan et al.

FOREIGN PATENT DOCUMENTS

| WO | WO 2003/031436 | 4/2003 |
| WO | WO 2007/050425 | 5/2007 |
| WO | WO 2011/107248 | 9/2011 |
| WO | WO 2012/064744 | 5/2012 |
| WO | WO 2013/064231 | 5/2013 |
| WO | WO2014/062938 | 4/2014 |
| WO | WO2015/035278 | 3/2015 |
| WO | WO2015/042212 | 3/2015 |
| WO | WO2015/103507 | 7/2015 |
| WO | WO2015/103508 | 7/2015 |
| WO | WO2015/103509 | 7/2015 |
| WO | WO2015/103510 | 7/2015 |

OTHER PUBLICATIONS

Asberom et al., Bioorganic & Mecicinal Chemistry Letters, vol. 17, No. 1, pp. 205-207 (2006).
Wang, Yao et al., Tetrahedron Letters, vol. 39, No. 52, pp. 9605-9608 (1998).
Ghorai, M. et al., Organic Letters, vol. 13, No. 16, pp. 4256-4259 (2011).
U.S. Appl. No. 15/148,209, filed May 6, 2016.

*Primary Examiner* — Brenda Coleman
(74) *Attorney, Agent, or Firm* — Elliott Korsen

(57) ABSTRACT

Described are RORγ modulators of the formula (I), or pharmaceutically acceptable salts thereof, wherein all substituents are defined herein. The invention includes stereoisomeric forms of the compounds of formula I, including stereoisomerically-pure, scalemic and racemic form, as well as tautomers thereof. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

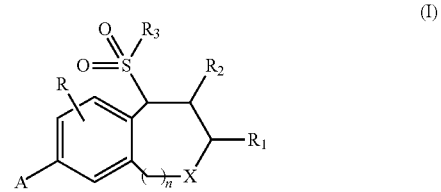

2 Claims, No Drawings

RORγ MODULATORS

CROSS-REFERENCE TO RELATED APPLICATIONS

This application claims the benefit of U.S. Provisional Application No. 61/880,391, filed Sep. 20, 2013, the disclosure of which is incorporated herein by reference in its entirety.

BACKGROUND OF THE INVENTION

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include psoriasis, arthritis, asthma, inflammatory bowel disease and multiple sclerosis.

The retinoid-related orphan receptors RORα, RORβ, and RORγ play an important role in numerous biological processes including organ development, immunity, metabolism, and circadian rhythms. See, for example, Dussault et al. in *Mech. Dev.* (1998) vol. 70, 147-153; Andre et al. in *EMBO J.* (1998) vol. 17, 3867-3877; Sun et al. in *Science* (2000) vol. 288, 2369-2373; and Jetten in *Nucl. Recept. Signal.* (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in *Biochem. Biophys. Res. Commun.* (1994) vol. 205, 1976-1983; Oritz et al. in *Mol. Endocrinol.* (1995) vol. 9, 1679-1691; and He et al. in *Immunity* (1998) vol. 9, 797-806. Expression of RORγt is restricted to lymphoid cell types including $CD4^+CD8^+$ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in *Science* (2000) vol. 288, 2369-2373; Ivanov et al. in *Cell* (2006) vol. 126, 1121-1133; Eberl et al. in *Nat. Immunol.* (2004) vol. 5, 64-73; Ivanov et al. in *Semin. Immunol.* (2007) vol. 19, 409-417; and Cua and Tato in *Nat. Rev. Immunol.* (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracelluar pathogens. See, for example, Ivanov et al. in *Semin. Immunol.* (2007) vol. 19: 409-417; and Marks and Craft in *Semin. Immunol.* (2009) vol. 21, 164-171. RORγ directly regulates IL-17 transcription and disruption of RORγ in mice attenuates IL-17 production. See, for example, Ivanov et al. in *Cell* (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in *Nat. Med.* (2002) vol. 8, 500-508; Tzartos et al. in *Am. J. Pathol.* (2008) vol. 172, 146-155; Kotake et al. in *J. Clin. Invest.* (1999) vol. 103, 1345-1352; Kirkham et al. in *Arthritis Rheum.* (2006) vol. 54, 1122-1131; Lowes et al. in *J. Invest. Dermatol.* (2008) vol. 128, 1207-1211; Leonardi et al. in *N. Engl. J. Med.* (2012) vol. 366, 1190-1199; Fujino et al. in *Gut* (2003) vol. 52, 65-70; Seiderer et al. in *Inflamm. Bowel Dis.* (2008) vol. 14, 437-445; Wong et al. in *Clin. Exp. Immunol.* (2001) vol. 125, 177-183; and Agache et al. in *Respir. Med.* (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in *Ann. N.Y. Acad. Sci.* (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in *Cell* (2006) vol. 126, 1121-1133; Yang et al. in *Immunity* (2008) vol. 28, 29-39; Pantelyushin et al. in *J. Clin. Invest.* (2012) vol. 122, 2252-2256; Leppkes et al. in *Gastroenterology* (2009) vol. 136, 257-267; and Tilley et al. in *J. Immunol.* (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

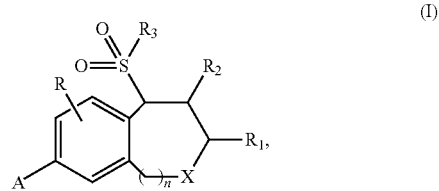

(I)

or pharmaceutically acceptable salts thereof, wherein all substituents are defined herein. The invention includes stereoisomeric forms of the compounds of formula I, including stereoisomerically-pure, scalemic and racemic form, as well as tautomers thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

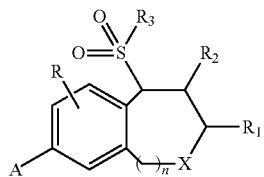
(I)

wherein:
X is O, S,

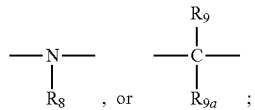

n is 0 or 1, provided that n is 1 when X is other than S;
A is

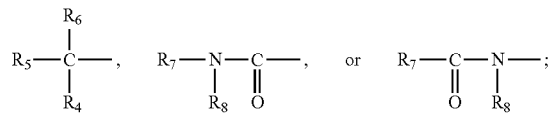

R is H, halo, optionally substituted halo-$C_1$-$C_6$-alkyl, OH, optionally substituted $C_1$-$C_4$ alkoxy, optionally substituted halo-$C_1$-$C_4$-alkoxy, CN, or optionally substituted $C_1$-$C_4$ alkyl;
$R_1$ is H, OH (where X is

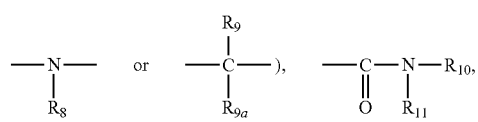

optionally substituted $C_1$-$C_4$ alkyl, optionally substituted halo-$C_1$-$C_4$-alkyl, or optionally substituted $C_1$-$C_4$ alkoxy-$C_1$-$C_4$ alkyl;

$R_2$ is

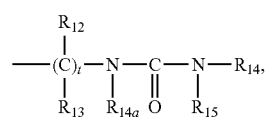
(1)

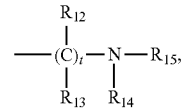
(2)

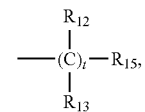
(3)

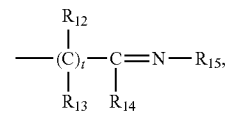
(4)

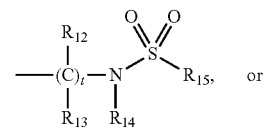
(5)

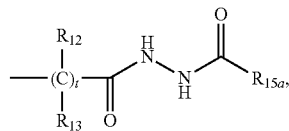
(6)

where q is 0, 1, 2, or 3, and t is 1, 2, or 3;
$R_3$ is optionally substituted aryl, optionally substituted 5- to 8-membered heteroaryl, optionally substituted $C_1$-$C_4$-alkyl-$C_6$-$C_{10}$-aryl, or optionally substituted $C_1$-$C_4$ alkyl 5- to 8-membered heteroaryl;
$R_4$ and $R_5$ are independently H, optionally substituted $C_1$-$C_4$ alkyl, optionally substituted $C_3$-$C_8$ cycloalkyl, optionally substituted arylsulfonyl, optionally substituted dideutero-$C_1$-$C_4$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted 5- to 7-membered monocyclic heteroaryl, optionally substituted 8- to 10-membered bicyclo heteroaryl, optionally substituted $C_2$-$C_6$ alkenyl, or optionally substituted $C_5$-$C_8$ cycloalkenyl,
provided that at least one of $R_4$ and $R_5$ is other than H, and only one of $R_4$ and $R_5$ can be hydroxy,
each $R_4$ and $R_5$ group being optionally substituted with 1 to 3 groups, or
$R_4$ and $R_5$ may be taken together with the nitrogen to which they are attached to form
(1) an optionally substituted 5- to 7-membered monocyclic heterocyclic ring optionally substituted with 1 or 2 halo groups, optionally substituted 1 or 2 $C_1$-$C_4$ alkyl groups, an optionally substituted $C_6$-$C_{10}$ aryl group, an optionally substituted 5- to 7-membered monocyclic heteroaryl (optionally substituted with $C_1$-$C_4$ alkyl), an optionally substituted $C_6$-$C_{10}$-aryl-$C_1$-$C_4$-alkyl group, an optionally substituted halo-$C_6$-$C_{10}$-aryl group, or an optionally substituted $C_3$-$C_8$-cycloalkyl-$C_1$-$C_4$-alkyl group, or (2) an optionally substituted 7- to 10-membered bicyclic heterocyclic ring optionally substituted with an aryl-$C_1$-$C_4$-alkyl group, or (3) an optionally substituted 5- to 7-membered monocyclic heteroaryl optionally substituted with $C_1$-$C_4$ alkyl;

$R_6$ is selected from hydroxy, optionally substituted $C_1$-$C_4$ alkyl, or optionally substituted halo-$C_1$-$C_4$-alkyl, provided that only one of $R_4$, $R_5$ and $R_6$ can be hydroxy;

$R_7$ and $R_8$ are independently selected from H, optionally substituted $C_1$-$C_4$ alkyl, optionally substituted $C_3$-$C_8$ cycloalkyl, or cyano;

$R_9$ and $R_{9a}$ are independently selected from H, halo, optionally substituted $C_1$-$C_4$ alkyl, optionally substituted $C_3$-$C_8$ cycloalkyl, or cyano;

$R_{10}$ and $R_{11}$ are independently selected from H, $C_1$-$C_4$ alkyl, or $C_3$-$C_8$ cycloalkyl, or $R_{10}$ and $R_{11}$ can be taken together to form a ring;

$R_{12}$ and $R_{13}$ are independently selected from H, optionally substituted $C_1$-$C_4$ alkyl, or optionally substituted $C_3$-$C_8$ cycloalkyl;

$R_{14}$, $R_{14a}$, and $R_{14b}$ are independently selected from H or optionally substituted $C_1$-$C_4$ alkyl; and $R_{15}$ and $R_{15a}$ are independently selected from optionally substituted $C_1$-$C_4$ alkyl, optionally substituted $C_1$-$C_4$ alkoxy, optionally substituted 5- to 8-membered heterocyclo, optionally substituted amino, optionally substituted $C_3$-$C_8$ cycloalkyl, optionally substituted $C_2$-$C_6$ alkynyl, optionally substituted 5- to 8-membered heteroaryl, optionally substituted $C_6$-$C_{10}$ aryl, or optionally substituted $C_6$-$C_{10}$ aryloxy, or $R_{14}$ and $R_{15}$ together with the N atom and/or C atom to which they are attached combine to form a cyclic ring which may be optionally substituted;

provided that both of $R_{14}$ and $R_{15}$ cannot be H, alkyl or haloalkyl;

and/or a pharmaceutically acceptable salt thereof, and/or stereoisomers thereof, and/or tautomers thereof.

In another aspect, there is provided a compound of Formula (II)

$$\text{(II)}$$

wherein:

X is $CH_2$ or S;

A is optionally substituted $C_1$-$C_4$ alkyl;

R is H;

$R_1$ is H;

$R_3$ is optionally substituted aryl or optionally substituted 5- to 8-membered heteroaryl;

$R_2$ is $$—(C)_t—N—C(=O)—N—R_{15}$$
with $R_{12}$, $R_{13}$, $R_{14a}$, $R_{14}$ substituents where $R_{14a}$ is H, $R_{14}$ is H, and $R_{15}$ is optionally substituted $C_3$-$C_8$ cycloalkyl, optionally substituted $C_6$-$C_{10}$ aryl, or optionally substituted $C_1$-$C_3$ alkyl;

or $R_2$ is $$—(C)_t—N—R_{15},$$
with $R_{12}$, $R_{13}$, $R_{14}$ substituents where $R_{14}$ is H, $R_{15}$ is optionally substituted $C_1$-$C_4$ alkyl, t is 1, 2 or 3, $R_{12}$ is H, and $R_{13}$ is H, or $R_2$ is $$—(C)_t—R_{15},$$
with $R_{12}$, $R_{13}$ substituents where $R_{15}$ is optionally substituted 5- to 8-membered heterocyclo or optionally substituted 5- to 8-membered heteroaryl, or $R_2$ is $$—(C)_t—C=N—R_{15},$$
with $R_{12}$, $R_{13}$, $R_{14}$ substituents where $R_{14}$ is optionally substituted $C_1$-$C_4$ alkyl, and $R_{15}$ is optionally substituted $C_6$-$C_{10}$ aryloxy or optionally substituted $C_1$-$C_4$ alkyl, t is 1, 2 or 3, $R_{12}$ is H, and $R_{13}$ is H, or $R_2$ is $$—(C)_t—N—S(=O)_2—R_{15},$$
with $R_{12}$, $R_{13}$, $R_{14}$ substituents where $R_{14}$ is H, $R_{15}$ is optionally substituted $C_3$-$C_6$ cycloalkyl, optionally substituted 5- to 8-membered heteroaryl, or optionally substituted $C_6$-$C_{10}$ aryl, t is 1, 2 or 3, $R_{12}$ is H, and $R_{13}$ is H or $R_2$ is $$—(C)_t—C(=O)—NH—NH—R_{15a},$$
with $R_{12}$, $R_{13}$ substituents where $R_{14}$ is H, $R_{15}$ is optionally substituted $C_3$-$C_6$ cycloalkyl, optionally substituted 5- to 8-membered heteroaryl, or optionally substituted $C_6$-$C_{10}$ aryl, t is 1, 2 or 3, $R_{12}$ is H, and $R_{13}$ is H;

t is 1, 2 or 3;

$R_{12}$ is H; and $R_{13}$ is H;

and/or a pharmaceutically acceptable salt thereof, and/or a stereoisomer thereof, and/or a tautomer thereof.

In another aspect, there are provided the following compounds:

(S)—N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-2-hydroxy-2-methylpropanehydrazide, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetonitrile, (S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-phenyl oxime, (S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime, (S,Z)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime, (S)-1,1,1,3,3,3-hexafluoro-2-(1-((4-fluorophenyl)sulfonyl)-2-((5-(methylthio)-1,3,4-thiadiazol-2-yl)methyl)-1,2,3,4-tetrahydroquinolin-6-yl)propan-2-ol, (S)-1,1,1,3,3,3-hexafluoro-2-(1-((4-fluorophenyl)sulfonyl)-2-((5-(methylsulfonyl)-1,3,4-thiadiazol-2-yl)methyl)-1,2,3,4-tetrahydroquinolin-6-yl)propan-2-ol, (S)-1,1,1,3,3,3-hexafluoro-2-(1-((4-fluorophenyl)sulfonyl)-2-((5-(2-hydroxypropan-2-yl)-1,3,4-oxadiazol-2-yl)methyl)-1,2,3,4-tetrahydroquinolin-6-yl)propan-2-ol, (S)-2-(2-((5-(2-amino-2-methylpropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol, (S)-3-amino-N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-3-methylbutanehydrazide, (S)—N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)isonicotinohydrazide, (S)-2-(2-((5-(1-aminocyclopropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol, (S)-1,1,1,3,3,3-hexafluoro-2-(1-((4-fluorophenyl)sulfonyl)-2-((5-(pyridin-4-yl)-1,3,4-oxadiazol-2-yl)methyl)-1,2,3,4-tetrahydroquinolin-6-yl)propan-2-ol, 2-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol, 1-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)butan-2-ol, (S)-1,1,1,3,3,3-hexafluoro-2-(2-((1-((4-fluorobenzyl)-1H-pyrazol-5-yl)methyl)-1-((4-fluorophenyl)sulfonyl)-1,2,3,4-tetrahydroquinolin-6-yl)propan-2-ol, 3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol, 3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol, 3-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol, (S)-benzyl 2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetate, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)-N,N-dimethylacetamide, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetamide, (S)-4-fluoro-N-((1-((4-fluorophenyl)sulfonyl)-6-(1,1,1,3,3,3-hexafluoro-2-hydroxypropan-2-yl)-1,2,3,4-tetrahydroquinolin-2-yl)methyl)benzenesulfonamide, (S)-6-chloro-N-((1-((4-fluorophenyl)sulfonyl)-6-(1,1,1,3,3,3-hexafluoro-2-hydroxypropan-2-yl)-1,2,3,4-tetrahydroquinolin-2-yl)methyl)pyridine-3-sulfonamide, (S)—N-((1-((4-fluorophenyl)sulfonyl)-6-(1,1,1,3,3,3-hexafluoro-2-hydroxypropan-2-yl)-1,2,3,4-tetrahydroquinolin-2-yl)methyl)cyclopropanesulfonamide, (S)-ethyl 2-(((1-((4-fluorophenyl)sulfonyl)-6-(1,1,1,3,3,3-hexafluoro-2-hydroxypropan-2-yl)-1,2,3,4-tetrahydroquinolin-2-yl)methyl)amino)acetate, (S)-2-(2-((benzylamino)methyl)-1-((4-fluorophenyl)sulfonyl)-1,2,3,4-tetrahydroquinolin-6-yl)-1,1,1,3,3,3-hexafluoropropan-2-ol, (±) 1-cyclopropyl-3-((1-((4-fluorophenyl)sulfonyl)-6-(1,1,1,3,3,3-hexafluoro-2-hydroxypropan-2-yl)-1,2,3,4-tetrahydroquinolin-2-yl)methyl)urea, (±) 1-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-3-phenylurea, and (±) 1-benzyl-3-((1-((4-fluorophenyl)sulfonyl)-6-(1,1,1,3,3,3-hexafluoro-2-hydroxypropan-2-yl)-1,2,3,4-tetrahydroquinolin-2-yl)methyl)urea, and/or a pharmaceutically acceptable salt thereof, and/or a stereoisomer thereof, and/or a tautomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

As noted above, each alkyl moiety (i.e., defined as "alkyl") is optionally substituted with one or more substituents (e.g., in various embodiments, from 1-5, from 1-3, from 1-2 or one) selected from the group consisting of -D, -halogen, —CN, —NO$_2$, —O—R$^{20}$, —N(R$^{21}$)$_2$ and —S(R$^{20}$), in which each R$^{20}$ is independently selected from the group consisting of —H, —CH$_3$, —CH$_2$CH$_3$ and —CF$_3$, and each R$^{21}$ is independently selected from the group consisting of —H, —CH$_3$ and —CH$_2$CH$_3$. In certain embodiments of the invention as described herein, each alkyl is optionally substituted with one or more substituents selected from the group consisting of -D, -halogen, —O—$R^{20}$ and —$N(R^{21})_2$ and —$S(R^{20})$, in which each $R^{20}$ is independently selected from the group consisting of —H, and —$CH_3$, and each $R^{21}$ is independently selected from the group consisting of —H and —$CH_3$. In other embodiments, each alkyl is optionally substituted with one or more substituents selected from the group consisting of -D, -halogen, —OH, —$NH_2$ and —SH. In other embodiments, each alkyl is unsubstituted.

As used herein, the "alkyl" groups are defined as having a given number of carbons. Accordingly, "$(C_1-C_4)$alkyl" is an alkyl group having from one to four carbons. An alkyl group can be branched or unbranched. Thus, "$(C_1-C_4)$alkyl" encompasses methyl, ethyl, n-propyl, isopropyl, n-butyl, sec-butyl and t-butyl, in unsubstituted and substituted forms as described above.

The term "fluoroalkyl" as used herein, means an alkyl group substituted with one or more fluorines and no other substituents. In certain embodiments, one or more carbons of the fluoroalkyl group is persubstituted with fluorine. Examples of fluoroalkyl moieties include, without limitation, fluoromethyl, difluromethyl, trifluoromethyl, pentafluoroethyl, 2,2,2-trifluoroethyl, and 1,1,1,3,3,3-hexafluoroisopropyl. "Fluoroalkyl" is encompassed within optionally-substituted alkyl as described above.

In general, any hydrogen atom of the compounds described herein (whether described explicitly as "—H" or as part of another moiety such as an alkyl or a phenyl) can be provided as a protium, or a deuterium. Thus, while deuterium is often described herein as a "substituent," the person of skill in the art will understand that deuterium can be used as the hydrogen atom species at any position in the compound. However, in certain embodiments of the compounds described herein, every hydrogen atom, unless otherwise explicitly specified, is a protium.

The term "deuteroalkyl" as used herein means an alkyl group substituted with one or more deuteria and no other substituents. Examples of "deuteroalkyl" include deuteromethyl and dideuteromethyl.

Individual compounds of certain embodiments of the present invention are provided One of skill in the art can adapt the reaction sequences of Schemes 1-50 to fit the desired target molecule. For example, use of a 2-ethylpyrimidine will result in compounds in which $R^1$ is ethyl, instead of methyl as in many of the example compounds. Similarly, while the schemes generally depict the -("B" ring system)-$(R^b)_y$ moiety as ortho-disubstituted phenyl, the person of skill will appreciate that use of different starting materials will provide different rings and/or different patterns of substitution. Of course, in certain situations one of skill in the art will use different reagents to affect one or more of the individual steps or to use protected versions of certain of the substituents. Additionally, one skilled in the art would recognize that compounds of structural formula (I) can be synthesized using different routes altogether.

The compounds of the present invention can be provided in a number of stereoisomeric forms. Accordingly, another aspect of the invention is a stereoisomeric form of a compound as described herein. For example, a compound of the present invention can be provided in racemic form. In other embodiments, a compound of the present invention is provided in scalemic form, or in a stereoisomerically pure form (e.g., substantially as a single enantiomer).

Another aspect of the invention is an N-oxide of a compound or stereoisomeric form as described herein.

Another aspect of the invention is a pharmaceutically acceptable salt of a compound, stereoisomeric form, or N-oxide as described herein. As used herein, the phrase "pharmaceutically acceptable salt" refers to both pharmaceutically acceptable acid and base addition salts. Such pharmaceutically acceptable salts include salts of acids such as hydrochloric, phosphoric, hydrobromic, sulfuric, sulfinic, formic, trifluoroacetic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Another aspect of the invention is a solvate or hydrate of a compound, stereoisomeric form, N-oxide or pharmaceutically acceptable salt as described herein. The person of skill in the art can determine whether a particular compound will form a solvate or a hydrate.

Another aspect of the invention is a pharmaceutical composition including a compound, stereoisomeric form, N-oxide, pharmaceutical salt, solvate or hydrate as described herein The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.*, 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2):159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology,* 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.*, 2012 August; 42(8):1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.*, 2012 Jun. 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factor T-bet and RORγt in mice," *Blood,* 2011 Nov. 3; 118(18):5011-20, which is hereby incorporated herein by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.,* 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.,* 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July:18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc. and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

Those experiments specifying that they were performed in a microwave oven were conducted in a SmithSynthesizer™ oven manufactured by Personal Chemistry or a Discover™ microwave oven manufactured by CEM corporation. The microwave ovens generate a temperature which can be selected to be between 60-250° C. The microwave ovens automatically monitor the pressure which is between 0-300 PSI. Reaction hold times and temperature set points are reported.

Abbreviations for HPLC Conditions:
Condition A: Chromolith SpeedROD 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$
Condition B: Column: Waters Xbridge C18, 19×150 mm, 5-µM particles; Guard Column: Mobile phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min
Condition C: Column: PursuitXRs C18 250×30 mm; 30 to 100% solvent B in solvent A, 20 min.; Solvent A=10% MeOH, 90% $H_2O$, 0.1% TFA; Solvent B=90% MeOH, 10% $H_2O$, 0.1% TFA.
Condition D: Column: Sunfire C18 3.5 um, 3.0×150 mm; (12 min); Solvent A=0.05% TFA in $H_2O$:MeCN (95:5); Solvent B=0.05% TFA in $H_2O$:MeCN (5:95)
Condition E: Column: YMC Combiscreen ODS-A 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$
Condition F: Column: Sunfire C18 3.5 um, 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$.
Condition G: Column: BEH C18 2.1×50 mm (4 min.); Solvent A=5% acetonitrile 95% $H_2O$, 10 mM $NH_4OAc$; Solvent A=95% acetonitrile 5% $H_2O$, 10 mM $NH_4Oac$
Condition H: Column: Low pH Col-1: Sunfire C18 3.5 um, 4.6×150 mm; Start % B=10; 12 Min. 100%; 15 Min. 100%; Flow Rate=1 mL/min; Wavelength1=220; Wavelength2=254; Solvent Pair=TFA-MeCN/$H_2O$; Solvent A=0.05% TFA in $H_2O$:MeCN (95:5); Solvent B=0.05% TFA in $H_2O$:MeCN (5:95); Column 1=LOW pH–Parallel HPLC; At 220 nm
Condition I: Column: Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient: 0-100% B over 25 minutes, then a 5-minute hold at 100% B; Flow: 20 mL/min.

Intermediates 1 and 2

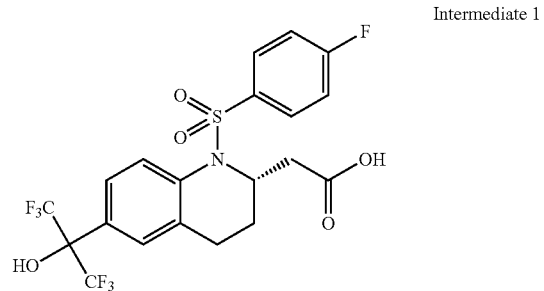

Intermediate 1

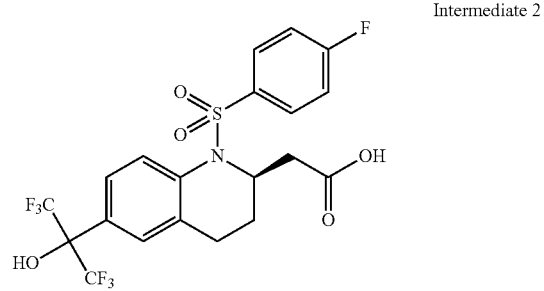

Intermediate 2

Step A: Tert-butyl 2-oxo-3,4-dihydroquinoline-1(2H)-carboxylate

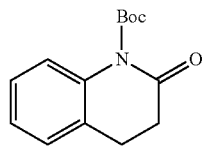 [SMILES: CC(C)(C)OC(=O)N1C(=O)CCc2ccccc21]

A mixture of 3,4-dihydroquinolin-2(1H)-one (8.46 g, 57.4 mmol), (BOC)$_2$O (13.3 mL, 57.4 mmol) and DMAP (0.702 g, 5.74 mmol) in acetonitrile (60 mL) was stirred at rt for 40 hrs and concentrated under vacuum. The residue was diluted with ethyl acetate (400 ml) and washed with 1N HCl (2×20 ml), water (20 ml), brine (20 ml), dried over anhydrous magnesium sulfate and concentrated under reduced pressure to afford tert-butyl 2-oxo-3,4-dihydroquinoline-1(2H)-carboxylate (13.5 g, 54.6 mmol, 95% yield). LC/MS M-t-Bu+1=192.1; $^1$H NMR (400 MHz, CDCl$_3$) δ ppm 7.39-7.14 (m, 2H), 7.14-7.04 (m, 1H), 6.96 (m, 1H), 3.11-2.87 (m, 2H), 2.80-2.62 (m, 2H), 1.62 (s, 9H).

Step B: Tert-butyl 2-hydroxy-3,4-dihydroquinoline-1(2H)-carboxylate

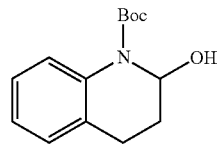 [SMILES: CC(C)(C)OC(=O)N1c2ccccc2CCC1O]

1.0 M THF solution of lithium triethylborohydride (65.5 mL, 65.5 mmol) was added dropwise to the solution of tert-butyl 2-oxo-3,4-dihydroquinoline-1(2H)-carboxylate (13.5 g, 54.6 mmol) in THF (200 mL) at −78° C. and stirred for 60 min. Saturated Na$_2$CO$_3$ (50 ml) was added and the contents warmed to −15° C. 30% H$_2$O$_2$ (50 ml) was then added dropwise. The resultant mixture was warmed to rt over a period of 1 hr and filtered. The filtrate was extracted with ethyl acetate (2×200 ml), washed with water, brine, dried over anhydrous magnesium sulfate and concentrated under reduced pressure to afford tert-butyl 2-hydroxy-3,4-dihydroquinoline-1(2H)-carboxylate (13.8 g) which was used as such for the next step without further purification. LC/MS M+Na=272.1; $^1$H-NMR (400 MHz, CD$_3$OD) δ ppm 7.49 (m, 1H), 7.17-7.07 (m, 1H), 7.05-6.88 (m, 1H), 5.96 (t, J=5.9 Hz, 1H), 2.83-2.68 (m, 1H), 2.62-2.49 (m, 1H), 2.26 (m, 1H), 1.89-1.65 (m, 2H), 1.57-1.48 (m, 9H).

Step C: Tert-butyl 2-(2-(benzyloxy)-2-oxoethyl)-3,4-dihydroquinoline-1(2H)-carboxylate

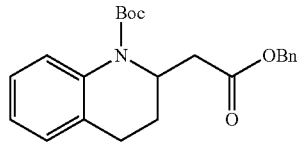 [SMILES: CC(C)(C)OC(=O)N1c2ccccc2CCC1CC(=O)OCc1ccccc1]

60% sodium hydride in mineral oil (3.88 g, 97 mmol) was added portion wise to a solution of benzyl 2-(dimethoxyphosphoryl)acetate (25.1 g, 97 mmol) in THF (200 mL) at 0° C. The resultant mixture was stirred at 0° C. for 1 hr. To this was added a solution of tert-butyl 2-hydroxy-3,4-dihydroquinoline-1(2H)-carboxylate (12.1 g, 48.5 mmol) in THF (100 ml) at 0° C. The resultant mixture was warmed to rt over 1 h, quenched with saturated aqueous NH$_4$Cl (100 ml) and extracted with ethyl acetate (2×200 ml). The combined organic layers were washed with water, brine, dried over anhydrous magnesium sulfate. Concentration under reduced pressure followed by purification by flash silica gel chromatography using a 10% mixture of ethyl acetate in hexane afforded tert-butyl 2-(2-(benzyloxy)-2-oxoethyl)-3,4-dihydroquinoline-1(2H)-carboxylate (13.8 g, 36.2 mmol, 75% yield). LC/MS (M+1): 382.3; $^1$H-NMR (400 MHz, CDCl$_3$) δ ppm 7.45 (d, J=8.1 Hz, 1H), 7.38-7.28 (m, 5H), 7.19-6.90 (m, 3H), 5.12-4.98 (m, 2H), 4.90 (m, 1H), 2.76-2.58 (m, 3H), 2.43 (m, 1H), 2.28 (m, 1H), 1.68-1.60 (m, 1H), 1.48 (s, 9H).

Step D: Benzyl 2-(1,2,3,4-tetrahydroquinolin-2-yl)acetate

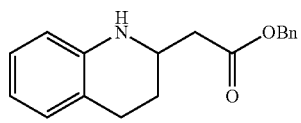 [SMILES: O=C(CC1CCc2ccccc2N1)OCc1ccccc1]

TFA (27.3 mL, 354 mmol) was added to a solution of tert-butyl 2-(2-(benzyloxy)-2-oxoethyl)-3,4-dihydroquinoline-1(2H)-carboxylate (13.5 g, 35.4 mmol) in DCM (50 mL) at rt, stirred for 2 hrs. and concentrated under vacuum. The residue was extracted with ethyl acetate (200 ml) washed with saturated aq. NaHCO$_3$, water, brine, dried over anhydrous magnesium sulfate and concentrated under reduced pressure to afford benzyl 2-(1,2,3,4-tetrahydroquinolin-2-yl)acetate (10.0 g, 35.5 mmol, 100% yield). LC/MS (M+1): 282.1; $^1$H-NMR (400 MHz, CDCl$_3$) δ ppm 7.37-7.31 (m, 1H), 7.27-7.18 (m, 2H), 7.19-7.07 (m, 3H), 7.06-6.78 (m, 2H), 6.61 (td, J=7.4, 0.9 Hz, 1H), 6.45 (d, J=7.9 Hz, 1H), 5.15 (s, 2H), 4.54-4.23 (m, 1H), 3.88-3.57 (m, 1H), 2.89-2.69 (m, 2H), 2.54 (m, 2H), 2.00-1.84 (m, 1H), 1.79-1.53 (m, 1H).

Step E: Benzyl 2-(6-(1,1,1,3,3,3-hexafluoro-2-hydroxypropan-2-yl)-1,2,3,4-tetrahydroquinolin-2-yl)acetate

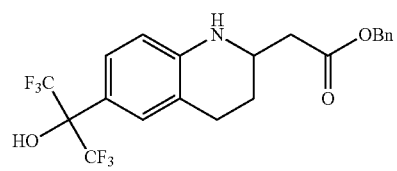

A mixture of benzyl 2-(1,2,3,4-tetrahydroquinolin-2-yl)acetate (10.0 g, 35.5 mmol), 1,1,1,3,3,3-hexafluoropropan-2-one, 1.5 H2O (4.47 mL, 39.1 mmol) and 4 Å molecular sieve (4 g) in Toluene (40 mL) was heated in a sealed tube at 120° C. for 7 hrs. The mixture was cooled to rt, filtered through a celite pad and washed with ethyl acetate. The filtrate was concentrated under vacuum. The residue was purified by flash silica gel chromatography using a 20% mixture of ethyl acetate in hexane to afford benzyl 2-(6-(1,1,1,3,3,3-hexafluoro-2-hydroxypropan-2-yl)-1,2,3,4-tetrahydroquinolin-2-yl)acetate (10.5 g, 23.5 mmol, 66% yield). LC/MS (M+1): 448.3; ¹H-NMR (400 MHz, CDCl₃) δ ppm 7.55-7.31 (m, 5H), 7.27-7.09 (m, 2H), 6.69-6.02 (m, 2H), 5.28-5.03 (m, 2H), 4.71 (br. s., 1H), 3.93-3.56 (m, 1H), 3.01-2.67 (m, 2H), 2.66-2.41 (m, 2H), 1.98 (m, 1H), 1.80-1.67 (m, 1H).

Step F: Benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate

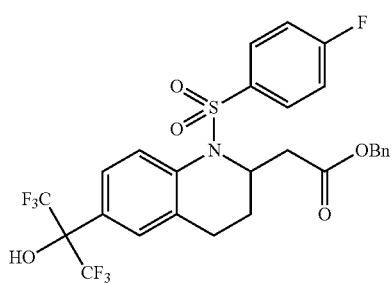 [SMILES: O=C(CC1CCc2cc(C(O)(C(F)(F)F)C(F)(F)F)ccc2N1S(=O)(=O)c1ccc(F)cc1)OCc1ccccc1]

A mixture of benzyl 2-(6-(1,1,1,3,3,3-hexafluoro-2-hydroxypropan-2-yl)-1,2,3,4-tetrahydroquinolin-2-yl)acetate (10.1 g, 22.6 mmol), 4-fluorobenzene-1-sulfonyl chloride (4.83 g, 24.8 mmol) and pyridine (7.30 mL, 90 mmol) in DCM (100 mL) was stirred at rt for 60 hrs and concentrated under vacuum. The residue was diluted with ethyl acetate (300 ml), washed with 1N HCl (2×30 ml), water (30 ml), brine (30 ml), dried over anhydrous magnesium sulfate, concentrated under reduced pressure and purified by flash silica gel chromatography using a 10% mixture of ethyl acetate in hexane to afford benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (10.2 g, 16.8 mmol, 75% yield). LC/MS (M+1): 606.3; ¹H-NMR (400 MHz, CDCl₃) δ ppm 7.78 (d, J=8.8 Hz, 1H), 7.56 (d, J=8.6 Hz, 1H), 7.54-7.44 (m, 2H), 7.44-7.33 (m, 5H), 7.26 (s, 1H), 7.11-6.93 (m, 2H), 5.32-4.98 (m, 2H), 4.76-4.59 (m, 1H), 3.62 (br. s., 1H), 2.89 (dd, J=15.4, 5.5 Hz, 1H), 2.67-2.36 (m, 2H), 1.99-1.71 (m, 2H), 1.53-1.40 (m, 1H).

Step G: (R)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate & (S)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate

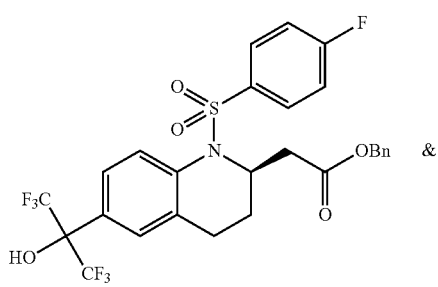

&

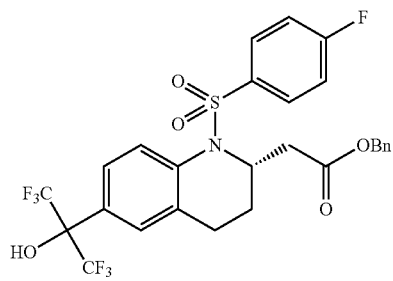

Racemic benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (10.2 g, 16.8 mmol) obtained above was separated into its homochiral components using a chiral Whelk-O1 (RR) column (46×25 cm, 5 um), 25% MeOH in CO₂, 3 ml/min, 35° C., 100 bars to afford: (R)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (3.90 g) as the first eluent off the column. The product had an HPLC ret. time=3.53 min. on the chiral column; >98.5% ee. (S)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (3.90 g) as the second eluent off the column. The product had an HPLC ret. time=4.07 min. on the chiral column; 98.2% ee. The absolute stereochemistry of the second eluting enantiomer was determined to be (S) based on a single crystal X-ray of the corresponding acid (step H-2), from the anomalous dispersion signal using the Flack method.

Step H-1: (R)-2-(1-((4-fluorophenyl)sulfonyl)-6-(1,1,3,3,3-hexafluoro-2-hydroxypropan-2-yl)-1,2,3,4-tetrahydroquinolin-2-yl)acetic acid

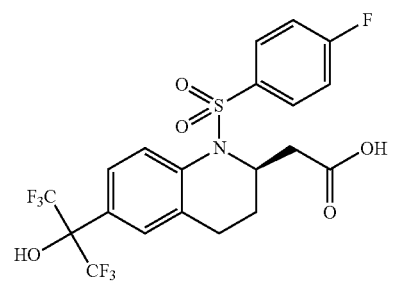 [SMILES: O=C(O)C[C@H]1CCc2cc(C(O)(C(F)(F)F)C(F)(F)F)ccc2N1S(=O)(=O)c1ccc(F)cc1]

A mixture of (R)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (0.088 g, 0.144 mmol) and 5% palladium on carbon (0.020 g, 0.009 mmol) in MeOH (5 mL) was stirred under a H₂ atmosphere at rt for 2 hrs and filtered. The filtrate was concentrated under vacuum to afford (R)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (0.074 g, 0.144 mmol, 100% yield). LC/MS (M+1): 516.2; ¹H-NMR (400 MHz, CDCl₃) δ ppm 7.98-7.69 (m, 1H), 7.69-7.52 (m, 3H), 7.43 (s, 1H), 7.30-7.12 (m, 2H), 4.73-4.58 (m, 1H), 2.86-2.64 (m, 1H), 2.63-2.43 (m, 2H), 2.07-1.86 (m, 2H), 1.65-1.54 (m, 1H).

Step H-2: Preparation of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid

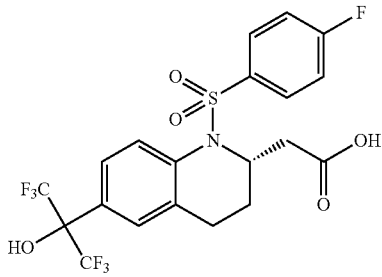 [SMILES: O=C(O)C[C@@H]1CCc2cc(C(O)(C(F)(F)F)C(F)(F)F)ccc2N1S(=O)(=O)c1ccc(F)cc1]

A mixture of (S)-benzyl 2-(1-((4-fluorophenyl)sulfonyl)-6-(1,1,1,3,3,3-hexafluoro-2-hydroxypropan-2-yl)-1,2,3,4-tetrahydroquinolin-2-yl)acetate (2.20 g, 3.63 mmol) and 5% palladium on carbon (0.387 g, 0.182 mmol) in MeOH (40 mL) was stirred under a H$_2$ atmosphere at rt for 4 hrs and filtered. The filtrate was concentrated under vacuum to afford (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (1.87 g, 3.63 mmol, 100% yield). LC/MS (M+1): 516.2; $^1$H-NMR (400 MHz, CDCl$_3$) δ ppm 7.98-7.69 (m, 1H), 7.69-7.52 (m, 3H), 7.43 (s, 1H), 7.30-7.12 (m, 2H), 4.73-4.58 (m, 1H), 2.86-2.64 (m, 1H), 2.63-2.43 (m, 2H), 2.07-1.86 (m, 2H), 1.65-1.54 (m, 1H).

Example 1

(S)—N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-2-hydroxy-2-methylpropanehydrazide

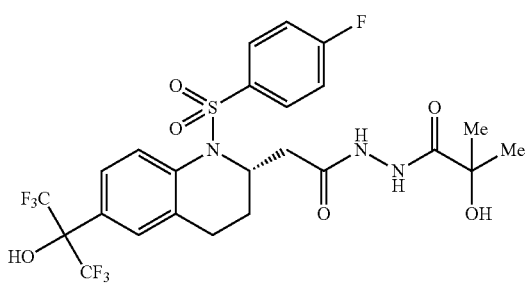 [SMILES: CC(C)(O)C(=O)NNC(=O)C[C@@H]1CCc2cc(C(O)(C(F)(F)F)C(F)(F)F)ccc2N1S(=O)(=O)c1ccc(F)cc1]

Step A: 5-(Aminomethyl)oxazolidin-2-one

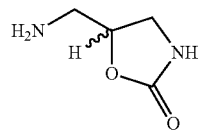

A solution of 5-(chloromethyl)oxazolidin-2-one (310 mg, 2.29 mmol) and sodium azide (297 mg, 4.57 mmol) in DMF (2 mL) was heated at 80° C. for 15 hrs. The reaction mixture was cooled to rt and DMF was removed under reduced pressure. To the residue was added MeOH (5 ml) and the contents stirred at rt for 1 hr and filtered. The filtrate was charged with 5% palladium on carbon (97 mg, 0.046 mmol) and stirred under an atmosphere of H$_2$ at 30 psi for 1 hr and filtered. Concentration of the filtrate provided 5-(Aminomethyl)oxazolidin-2-one (0.270 g) which was used as such for the next step without purification. $^1$H-NMR (400 MHz, CD$_3$OD) δ ppm 4.72-4.62 (m, 1H), 3.75-3.63 (m, 1H), 3.44-3.34 (m, 1H), 2.99-2.87 (m, 2H).

Step B: (S)—N'-(2-1-((4-fluorophenyl)sulfonyl)-6-(1,1,1,3,3,3-hexafluoro-2-hydroxypropan-2-yl)-1,2,3,4-tetrahydroquinolin-2-yl)-acetyl)-2-hydroxy-2-methylpropanehydrazide

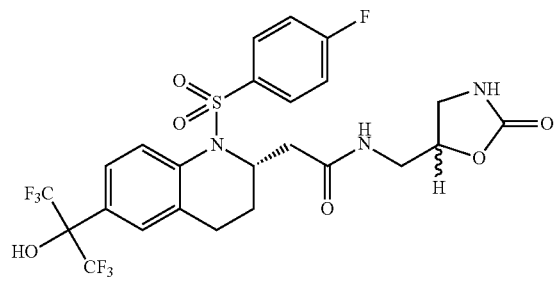 [SMILES: O=C(C[C@@H]1CCc2cc(C(O)(C(F)(F)F)C(F)(F)F)ccc2N1S(=O)(=O)c1ccc(F)cc1)NCC1CNC(=O)O1]

To a solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (intermediate 1, 14 mg, 0.027 mmol) in DMF was added DIEA, BOP and 2-hydroxy-2-methylpropanehydrazide (6.42 mg, 0.054 mmol). The reaction mixture was stirred at rt for 1 h and purified by preparative HPLC (condition C) to yield the title compound (11 mg, 0.016 mmol, 59% yield). LC/MS (M+1): 616.0; $^1$H-NMR (400 MHz, CD$_3$OD) δ ppm 7.79 (d, J=8.8 Hz, 1H), 7.70-7.55 (m, 2H), 7.45 (s, 1H), 7.31-7.10 (m, 2H), 4.78-4.63 (m, 1H), 2.77-2.68 (m, 1H), 2.68-2.56 (m, 1H), 2.45 (m, 1H), 1.98-1.85 (m, 1H), 1.73-1.63 (m, 1H), 1.41 (m, 6H).

Example 2

(S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetonitrile

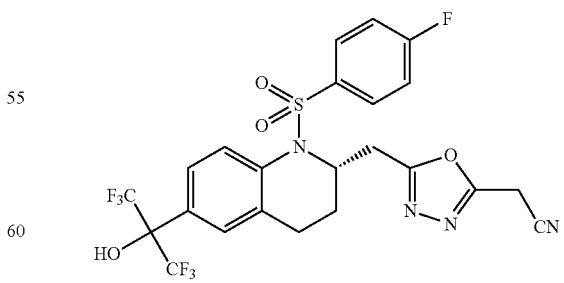

To a solution of (S)-2-(1-((4-fluorophenyl)sulfonyl)-6-(1,1,3,3,3-hexafluoro-2-hydroxypropan-2-yl)-1,2,3,4-tetrahydroquinolin-2-yl)acetic acid (15 mg, 0.029 mmol) in DMF (0.8 mL) were added 2-cyanoacetohydrazide (2.88 mg, 0.029 mmol), ((1H-benzo[d][1,2,3]triazol-1-yl)oxy)tris(dimethylamino)phosphonium hexafluorophosphate(V) (19.31 mg, 0.044 mmol) and N-ethyl-N-isopropylpropan-2-amine (7.52 mg, 0.058 mmol). The resulting mixture was stirred at rt for 1 h. It was purified by preparative HPLC to provide the intermediate acyl hydrazide (10 mg), which was treated with POCl₃ (0.3 mL, 3.22 mmol) and heated to 90° C. for 1.5 hr. The reaction mixture was cooled to rt, and carefully quenched with saturated NaHCO₃ (3 ml) and extracted with DCM (3×30 ml). The combined organic layers were washed with brine, dried (MgSO₄) and concentrated under vacuum. The residue was purified by preparative HPLC (condition C) to provide the title compound (1.2 mg, 0.002 mmol, 7% yield). LC/MS (M+1): 579.0; ¹H-NMR (500 MHz, 1 to 1 mixture of CDCl₃ and CD₃OD) δ ppm 7.78 (d, J=8.9 Hz, 1H), 7.65 (d, J=7.9 Hz, 1H), 7.50-7.34 (m, 3H), 7.12 (t, J=8.4 Hz, 2H), 4.80-4.69 (m, 3H), 3.22 (d, J=6.4 Hz, 2H), 2.53 (m, 1H), 2.21-2.03 (m, 1H), 1.85-1.73 (m, 1H), 1.65-1.41 (m, 1H).

Example 3

(S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-phenyl oxime

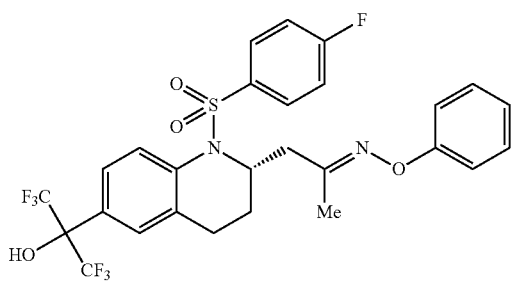 [SMILES: C/C(C[C@@H]1CCc2cc(C(O)(C(F)(F)F)C(F)(F)F)ccc2N1S(=O)(=O)c1ccc(F)cc1)=N\Oc1ccccc1]

Step A: (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-N-methoxy-N-methylacetamide

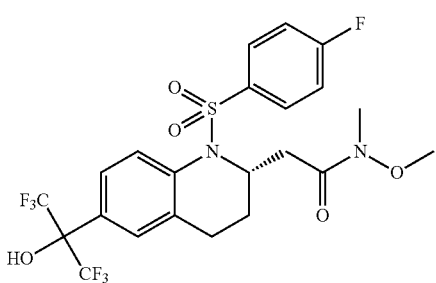 [SMILES: CON(C)C(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (40 mg, 0.078 mmol) was treated with N,O-dimethylhydroxylamine, HCl (15.1 mg, 0.155 mmol) to provide (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-N-methoxy-N-methylacetamide (35 mg, 0.063 mmol, 81% yield). LC/MS (M+1): 559.0; ¹H-NMR (400 MHz, CD₃OD) δ ppm 7.93-7.72 (m, 2H), 7.68-7.42 (m, 3H), 7.21 (t, J=8.7 Hz, 2H), 4.81-4.59 (m, 1H), 3.63 (s, 3H), 3.20 (s, 3H), 2.93-2.89 (m, 1H), 2.72-2.46 (m, 2H), 2.08-1.73 (m, 2H), 1.64-1.51 (m, 1H).

Step B: (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one

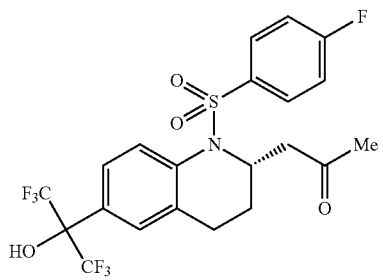 [SMILES: CC(=O)C[C@@H]1CCc2cc(C(O)(C(F)(F)F)C(F)(F)F)ccc2N1S(=O)(=O)c1ccc(F)cc1]

3.0 M ether solution of methylmagnesium bromide (0.104 mL, 0.313 mmol) was added to the mixture of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)-N-methoxy-N-methylacetamide (35 mg, 0.063 mmol) in THF (1 mL) at 0° C. and stirred for 1 hr. It was quenched with saturated NH₄Cl (2 ml), extracted with ethyl acetate (60 ml), washed with water, brine, dried (MgSO₄) and concentrated under reduced pressure. The residue was purified by flash silica gel chromatography using a 30% mixture of ethyl acetate in hexane to afford (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one (27 mg, 0.047 mmol, 76% yield). LC/MS (M+1): 514.0; ¹H-NMR (400 MHz, CD₃OD) δ ppm 7.77 (m, 1H), 7.66-7.52 (m, 3H), 7.43 (s, 1H), 7.29-7.10 (m, 2H), 4.77-4.67 (m, 1H), 2.94-2.68 (m, 2H), 2.61-2.47 (m, 1H), 2.17 (s, 3H), 2.01-1.80 (m, 2H), 1.56-1.40 (m, 1H).

Step C: (S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-phenyl oxime

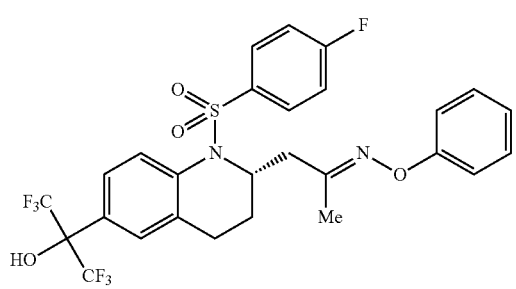 [SMILES: C/C(C[C@@H]1CCc2cc(C(O)(C(F)(F)F)C(F)(F)F)ccc2N1S(=O)(=O)c1ccc(F)cc1)=N\Oc1ccccc1]

The mixture of (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one (12 mg, 0.023 mmol) and O-phenylhydroxylamine, HCl (10.2 mg, 0.070 mmol) in EtOH (1 mL) was stirred at rt for 15 hrs and purified by preparative HPLC (condition C) to provide the title compound (10.3 mg, 0.017 mmol, 71% yield). LC/MS (M+1): 605.0; $^1$H-NMR (500 MHz, 1 to 1 mixture of CDCl$_3$ and CD$_3$OD) δ ppm 7.79 (d, J=8.9 Hz, 1H), 7.67-7.61 (m, 1H), 7.58-7.49 (m, 2H), 7.46 (s, 1H), 7.33-7.23 (m, 2H), 7.15-7.03 (m, 4H), 6.99 (t, J=7.2 Hz, 1H), 4.69-4.58 (m, 1H), 2.77-2.54 (m, 2H), 2.50 (m, 1H), 2.15 (s, 3H), 2.10-1.99 (m, 1H), 1.95-1.83 (m, 1H), 1.72-1.52 (m, 1H).

Examples 4 & 5

(S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime and (S,Z)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime

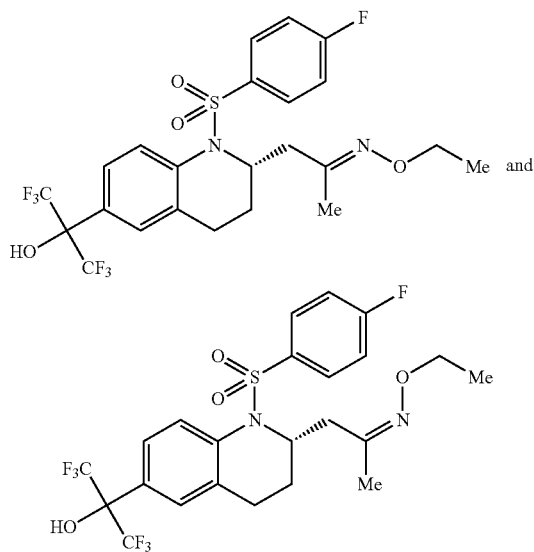

Following similar procedure as in Step B of Example 3, (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one (Ex. 3, step B, 12 mg, 0.023 mmol) was treated with O-ethylhydroxylamine, HCl (6.84 mg, 0.070 mmol to provide (S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime (7.8 mg, 0.014 mmol, 60% yield). LC/MS (M+1): 557.0; $^1$H-NMR (500 MHz, 1 to 1 mixture of CDCl$_3$ and CD$_3$OD) δ ppm 7.78 (d, J=8.9 Hz, 1H), 7.65-7.59 (m, 1H), 7.54-7.45 (m, 2H), 7.42-7.33 (m, 1H), 7.20-7.03 (m, 2H), 4.62-4.48 (m, 1H), 4.03 (q, J=6.9 Hz, 2H), 2.68-2.45 (m, 2H), 2.35 (m, 1H), 2.09-1.97 (m, 1H), 1.95 (s, 3H), 1.80 (m, 1H), 1.55 (m, 1H), 1.29-1.16 (m, 3H). (S,Z)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime (2.7 mg, 0.0049 mmol, 21% yield). LC/MS (M+1): 557.0; $^1$H-NMR (500 MHz, 1 to 1 mixture of CDCl$_3$ and CD$_3$OD) δ ppm. 79 (d, J=8.9 Hz, 1H), 7.64-7.58 (m, 1H), 7.58-7.48 (m, 2H), 7.45 (s, 1H), 7.33-7.04 (m, 2H), 4.85-4.73 (m, 1H), 4.16-3.93 (m, 2H), 2.71-2.60 (m, 2H), 2.52 (m, 1H), 2.13 (m, 1H), 1.94 (s, 3H), 1.84-1.69 (m, 1H), 1.65-1.44 (m, 1H), 1.17 (t, J=7.2 Hz, 3H).

Example 6

(S)-1,1,1,3,3,3-hexafluoro-2-(1-((4-fluorophenyl)sulfonyl)-2-((5-(methylthio)-1,3,4-thiadiazol-2-yl)methyl)-1,2,3,4-tetrahydroquinolin-6-yl)propan-2-ol

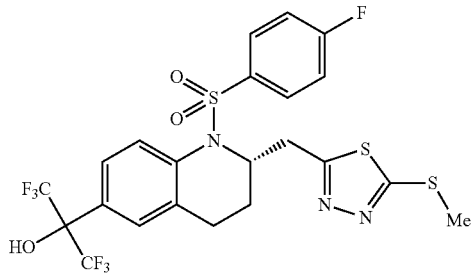 [SMILES: CSc1nnc(C[C@@H]2CCc3cc(C(O)(C(F)(F)F)C(F)(F)F)ccc3N2S(=O)(=O)c2ccc(F)cc2)s1]

Step A: (S)-methyl 2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)hydrazinecarbodithioate

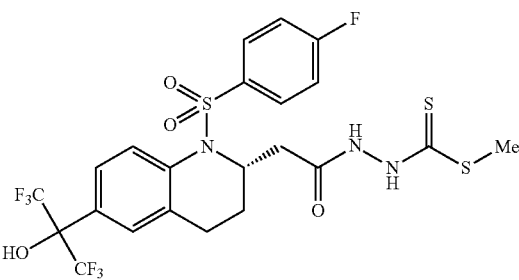 [SMILES: CSC(=S)NNC(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (63 mg, 0.122 mmol) was treated with methyl hydrazinecarbodithioate (22.4 mg, 0.183 mmol) to provide (S)-methyl 2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)hydrazinecarbodithioate (66 mg, 0.107 mmol, 87% yield). LC/MS (M+1): 619.9; $^1$H-NMR (400 MHz, CD$_3$OD) δ ppm 7.80 (d, J=8.6 Hz, 1H), 7.60 (d, J=7.9 Hz, 3H), 7.49-7.39 (m, 1H), 7.29-7.15 (m, 2H), 3.00 (s, 3H), 2.75-2.43 (m, 4H), 2.10-1.99 (m, 1H), 1.96-1.85 (m, 1H), 1.77-1.53 (m, 1H).

Step B: (S)-1,1,1,3,3,3-hexafluoro-2-(1-((4-fluorophenyl)sulfonyl)-2-((5-(methylthio)-1,3,4-thiadiazol-2-yl)methyl)-1,2,3,4-tetrahydroquinolin-6-yl)propan-2-ol

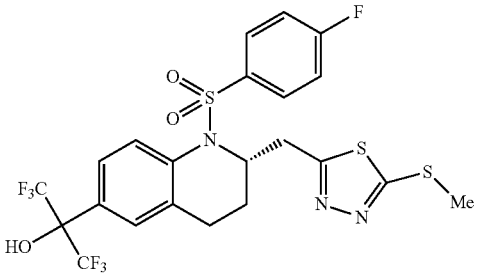 [SMILES: CSc1nnc(C[C@@H]2CCc3cc(C(O)(C(F)(F)F)C(F)(F)F)ccc3N2S(=O)(=O)c2ccc(F)cc2)s1]

Tosic acid (8.44 mg, 0.044 mmol) was added to the solution of (S)-methyl 2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)hydrazinecarbodithioate (55 mg, 0.089 mmol) in toluene (1 mL) at rt and heated to 110° C. for 1 hr. The mixture was cooled to rt, concentrated under reduced pressure and purified by flash silica gel chromatography using a 40% mixture of ethyl acetate in hexane to provide the title compound (38 mg, 0.057 mmol, 64% yield). LC/MS (M+1): 601.9; $^1$H-NMR (400 MHz, CDCl$_3$) δ ppm 7.85 (d, J=8.8 Hz, 1H), 7.60 (d, J=8.4 Hz, 1H), 7.51-7.40 (m, 2H), 7.36 (s, 1H), 7.04 (t, J=8.5 Hz, 2H), 4.61 (quin, J=6.4 Hz, 1H), 3.41-3.18 (m, 2H), 2.73 (s, 3H), 2.60-2.42 (m, 1H), 1.97-1.85 (m, 2H), 1.69-1.59 (m, 1H).

Example 7

(S)-1,1,1,3,3,3-hexafluoro-2-(1-((4-fluorophenyl)sulfonyl)-2-((5-(methylsulfonyl)-1,3,4-thiadiazol-2-yl)methyl)-1,2,3,4-tetrahydroquinolin-6-yl)propan-2-ol

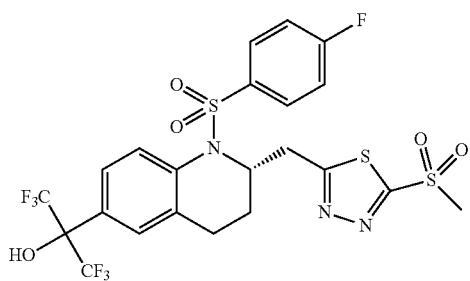 [SMILES: CS(=O)(=O)c1nnc(C[C@@H]2CCc3cc(C(O)(C(F)(F)F)C(F)(F)F)ccc3N2S(=O)(=O)c2ccc(F)cc2)s1]

mCPBA (30.1 mg, 0.175 mmol) was added to a solution of (S)-1,1,1,3,3,3-hexafluoro-2-(1-((4-fluorophenyl)sulfonyl)-2-((5-(methylthio)-1,3,4-thiadiazol-2-yl)methyl)-1,2,3,4-tetrahydroquinolin-6-yl)propan-2-ol (Ex. 6, 35 mg, 0.058 mmol) in DCM (2 mL) at rt and stirred for 2 hrs. The reaction mixture was quenched with saturated NaHCO$_3$ (2 ml) and extracted with ethyl acetate (60 ml). The ethyl acetate layer was washed with water, brine, dried (MgSO$_4$), concentrated under reduced pressure and purified by flash silica gel chromatography using a 40% mixture of ethyl acetate in hexane to provide the title compound (30 mg, 0.043 mmol, 73% yield). LC/MS (M+1): 633.9; $^1$H-NMR (400 MHz, CDCl$_3$) δ ppm 7.87 (d, J=8.6 Hz, 1H), 7.64 (d, J=8.8 Hz, 1H), 7.52-7.32 (m, 3H), 7.15-6.91 (m, 2H), 4.65 (m, 1H), 3.67-3.45 (m, 2H), 3.43 (s, 3H), 2.53 (m, 1H), 2.04-1.82 (m, 2H), 1.65-1.52 (m, 1H).

Example 8

(S)-1,1,1,3,3,3-hexafluoro-2-(1-((4-fluorophenyl)sulfonyl)-2-((5-(2-hydroxypropan-2-yl)-1,3,4-oxadiazol-2-yl)methyl)-1,2,3,4-tetrahydroquinolin-6-yl)propan-2-ol

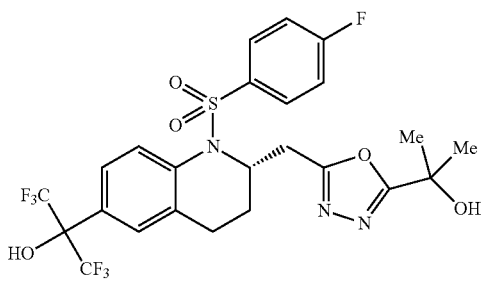 [SMILES: CC(C)(O)c1nnc(C[C@@H]2CCc3cc(C(O)(C(F)(F)F)C(F)(F)F)ccc3N2S(=O)(=O)c2ccc(F)cc2)o1]

Step A: (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide

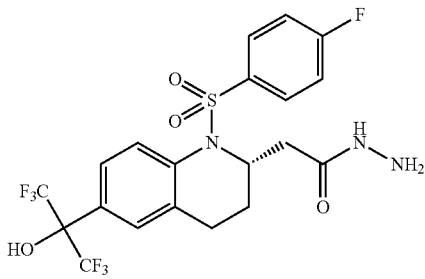 [SMILES: NNC(=O)C[C@@H]1CCc2cc(C(O)(C(F)(F)F)C(F)(F)F)ccc2N1S(=O)(=O)c1ccc(F)cc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (102 mg, 0.198 mmol) was treated with hydrazine (0.099 mL, 3.17 mmol) to provide (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (99 mg, 0.187 mmol, 94% yield). LC/MS (M+1): 530.1; $^1$H-NMR (400 MHz, CD$_3$OD) δ ppm 7.78 (d, J=8.8 Hz, 1H), 7.67-7.53 (m, 3H), 7.44 (s, 1H), 7.31-7.07 (m, 2H), 4.79-4.62 (m, 1H), 2.62-2.43 (m, 2H), 2.32 (m, 1H), 2.12-1.95 (m, 1H), 1.94-1.79 (m, 1H), 1.59-1.49 (m, 1H).

Step B: (S)-ethyl 5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazole-2-carboxylate

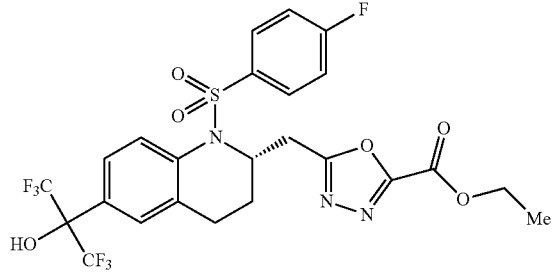 [SMILES: CCOC(=O)c1nnc(C[C@@H]2CCc3cc(C(O)(C(F)(F)F)C(F)(F)F)ccc3N2S(=O)(=O)c2ccc(F)cc2)o1]

Ethyl 2-chloro-2-oxoacetate (4.26 mg, 0.031 mmol) was added to the solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (15 mg, 0.028 mmol) and DIEA (0.015 ml, 0.085 mmol) in DCM (1 ml) and THF (0.5 mL) at 0° C. The resultant mixture was warmed to rt and stirred for 3 hrs. Then tosyl-Cl (5.94 mg, 0.031 mmol) was added and the contents stirred at rt for 15 hrs. The mixture was diluted with ethyl acetate (60 ml), washed with saturated aq. NaHCO$_3$, water, brine, dried (MgSO$_4$) and concentrated under reduced pressure. The residue was purified by flash silica gel chromatography using a 30% mixture of ethyl acetate in hexane to provide (S)-ethyl 5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazole-2-carboxylate (12 mg, 0.018 mmol, 62% yield). LC/MS (M+1): 612.2; $^1$H-NMR (400 MHz, CDCl₃) δ ppm 7.83 (d, J=8.6 Hz, 1H), 7.61 (d, J=8.6 Hz, 1H), 7.59-7.43 (m, 2H), 7.38 (s, 1H), 7.14-6.93 (m, 2H), 4.73 (quin, J=6.9 Hz, 1H), 4.52 (q, J=7.0 Hz, 2H), 3.77 (s, 1H), 3.38 (m, 1H), 3.21 (m, 1H), 2.51 (m, 1H), 2.13-1.97 (m, 1H), 1.88-1.74 (m, 1H), 1.62-1.54 (m, 1H), 1.47 (t, J=7.2 Hz, 3H).

Step C: (S)-1,1,1,3,3,3-hexafluoro-2-(1-((4-fluorophenyl)sulfonyl)-2-((5-(2-hydroxypropan-2-yl)-1,3,4-oxadiazol-2-yl)methyl)-1,2,3,4-tetrahydroquinolin-6-yl)propan-2-ol

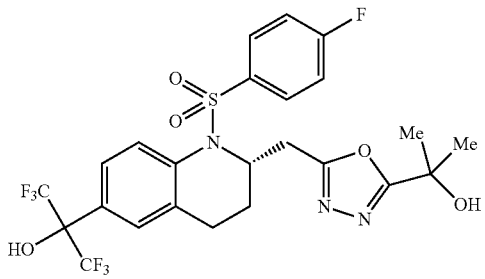 [SMILES: CC(C)(O)c1nnc(C[C@@H]2CCc3cc(C(O)(C(F)(F)F)C(F)(F)F)ccc3N2S(=O)(=O)c2ccc(F)cc2)o1]

3.0 M ether solution of methylmagnesium bromide (0.022 mL, 0.065 mmol) was added to a solution of (S)-ethyl 5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazole-2-carboxylate (8 mg, 0.013 mmol) in THF (0.5 mL) at 0° C. and stirred for 30 min. It was quenched with saturated NH₄Cl, diluted with ethyl acetate (60 ml), washed with water, brine, dried (MgSO₄) and concentrated under reduced pressure. The residue was purified by flash silica gel chromatography using a 60% mixture of ethyl acetate in hexane to provide the title compound (2.8 mg, 0.0004 mmol, 32% yield). LC/MS (M+1): 598.3; ¹H-NMR (400 MHz, CD₃OD) δ ppm 7.76 (d, J=8.6 Hz, 1H), 7.61 (d, J=9.0 Hz, 1H), 7.60-7.48 (m, 2H), 7.44 (s, 1H), 7.22-7.13 (m, 2H), 4.79-4.72 (m, 1H), 3.28-3.20 (m, 1H), 3.21-3.10 (m, 1H), 2.55 (m, 1H), 2.14-2.06 (m, 1H), 1.89-1.79 (m, 1H), 1.77-1.56 (m, 7H).

Examples 9 and 10

(S)-2-(2-((5-(2-amino-2-methylpropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol (S)-3-amino-N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-3-methylbutanehydrazide

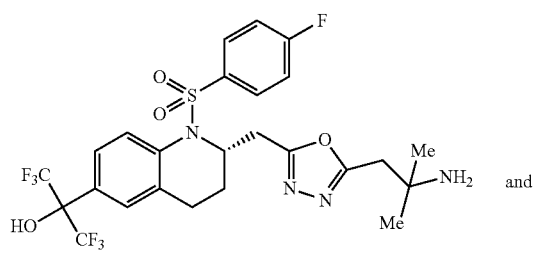

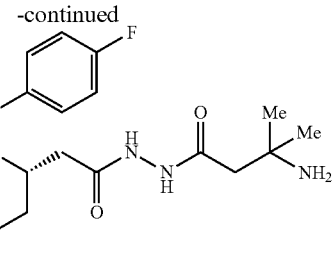

Step A: (S)-tert-butyl (4-(2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)hydrazinyl)-2-methyl-4-oxobutan-2-yl)carbamate

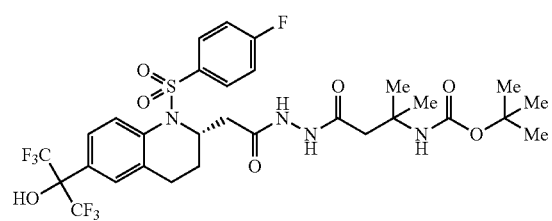 [SMILES: CC(C)(CC(=O)NNC(=O)C[C@@H]1CCc2cc(C(O)(C(F)(F)F)C(F)(F)F)ccc2N1S(=O)(=O)c1ccc(F)cc1)NC(=O)OC(C)(C)C]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (20 mg, 0.038 mmol) was treated with 3-((tert-butoxycarbonyl)amino)-3-methylbutanoic acid (12.3 mg, 0.057 mmol) to provide (S)-tert-butyl (4-(2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)hydrazinyl)-2-methyl-4-oxobutan-2-yl)carbamate (23 mg, 0.032 mmol, 84% yield). LC/MS (M+1): 729.4; ¹H-NMR (400 MHz, CD₃OD) δ ppm 7.86-7.73 (m, 1H), 7.70-7.55 (m, 3H), 7.49-7.38 (m, 1H), 7.30-6.94 (m, 2H), 4.80-4.63 (m, 1H), 2.79-2.64 (m, 1H), 2.63-2.51 (m, 2H), 2.44 (m, 1H), 1.96-1.77 (m, 2H), 1.68-1.48 (m, 2H), 1.47-1.32 (m, 15H).

Step B: (S)-2-(2-((5-(2-amino-2-methylpropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol & (S)-3-amino-N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-3-methylbutanehydrazide

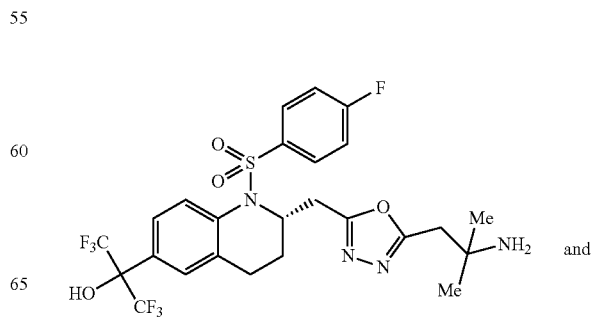

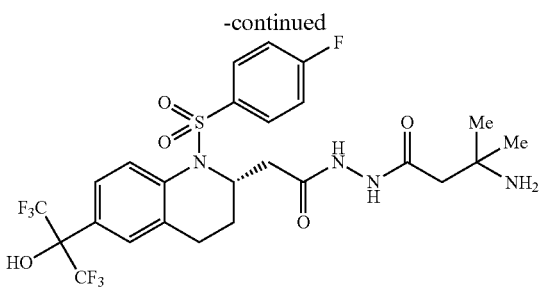

To a solution of (S)-tert-butyl (4-(2-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)hydrazinyl)-2-methyl-4-oxobutan-2-yl)carbamate (13 mg, 0.018 mmol) in DCM (1 mL) were added DIEA (9.35 µl, 0.054 mmol) and Ts-Cl (10.2 mg, 0.054 mmol). The resulting mixture was stirred at rt for 15 hrs. The mixture was diluted with ethyl acetate (60 ml), washed with water, brine, dried (MgSO$_4$) and concentrated by vacuum. The residue was dissolved in DCM (1 mL) and TFA (0.2 mL, 2.60 mmol) was added. The resultant mixture was stirred at rt for 1 hr and concentrated under reduced pressure. The residue was purified by preparative HPLC to provide (S)-2-(2-((5-(2-amino-2-methylpropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol (3.3 mg, 0.0004 mmol, 23% yield). LC/MS (M+1): 611.2; $^1$H-NMR (400 MHz, CD$_3$OD) δ ppm 7.78 (d, J=8.8 Hz, 1H), 7.63 (d, J=8.6 Hz, 1H), 7.57-7.41 (m, 3H), 7.28-7.08 (m, 2H), 4.82-4.67 (m, 1H), 3.26-3.20 (m, 1H), 3.16-3.05 (m, 1H), 2.65-2.52 (m, 1H), 2.13-2.05 (m, 1H), 1.95-1.84 (m, 1H), 1.77-1.63 (m, 1H), 1.55-1.43 (m, 6H). and (S)-3-amino-N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-3-methylbutanehydrazide (5.0 mg, 0.0006 mmol, 34% yield). LC/MS (M+1): 629.3; $^1$H-NMR (400 MHz, CD$_3$OD) δ ppm 7.81 (d, J=8.8 Hz, 1H), 7.66-7.54 (m, 3H), 7.44 (s, 1H), 7.20 (t, J=8.7 Hz, 2H), 4.83-4.70 (m, 1H), 2.77-2.58 (m, 2H), 2.47 (m, 1H), 2.01-1.81 (m, 2H), 1.68-1.57 (m, 1H), 1.49-1.36 (m, 6H).

Example 11

(S)—N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)isonicotinohydrazide

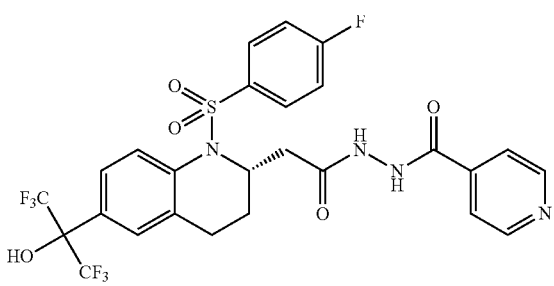 [SMILES: O=C(C[C@@H]1CCc2cc(C(O)(C(F)(F)F)C(F)(F)F)ccc2N1S(=O)(=O)c1ccc(F)cc1)NNC(=O)c1ccncc1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (15 mg, 0.029 mmol) was treated with isonicotinohydrazide (5.99 mg, 0.044 mmol) to provide the title compound (17 mg, 0.022 mmol, 74% yield). LC/MS (M+1): 635.3; $^1$H-NMR (400 MHz, CD$_3$OD) δ ppm 8.89 (d, J=4.6 Hz, 2H), 8.13 (d, J=6.4 Hz, 2H), 7.83 (d, J=8.8 Hz, 1H), 7.60 (dd, J=8.8, 5.3 Hz, 3H), 7.46 (s, 1H), 7.20 (t, J=8.7 Hz, 2H), 4.84-4.67 (m, 1H), 2.79 (m, 1H), 2.70-2.45 (m, 2H), 2.13-1.86 (m, 2H), 1.69 (m, 1H).

Example 12

(S)-2-(2-((5-(1-aminocyclopropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol

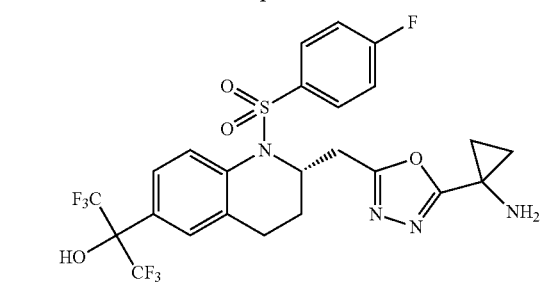

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (Ex. 8, step A, 15 mg, 0.028 mmol) was treated with 1-((tert-butoxycarbonyl)amino)cyclopropanecarboxylic acid (8.55 mg, 0.042 mmol) to provide the expected coupled product (19 mg) which was dissolved in toluene (1 mL). Tosic acid (5.39 mg, 0.028 mmol) was added and the reaction mixture was heated to 110° C. in a sealed tube for 2 hrs, cooled to rt and purified by preparative HPLC (condition C) to afford the title compound (1.9 mg, 0.0003 mmol, 11% yield). LC/MS (M+1): 595.2; $^1$H-NMR (500 MHz, DMSO-d$_6$) δ ppm 7.83-7.64 (m, 3H), 7.54 (d, J=9.4 Hz, 1H), 7.49-7.29 (m, 3H), 4.85 (m, 1H), 2.83-2.62 (m, 3H), 2.19 (m, 1H), 1.87 (m, 1H), 1.76-1.66 (m, 1H), 1.57-1.48 (m, 2H), 1.41-1.28 (m, 2H).

Example 13

(S)-1,1,1,3,3,3-hexafluoro-2-(1-((4-fluorophenyl)sulfonyl)-2-((5-(pyridin-4-yl)-1,3,4-oxadiazol-2-yl)methyl)-1,2,3,4-tetrahydroquinolin-6-yl)propan-2-ol

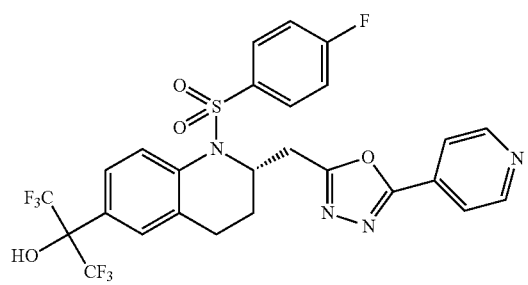 [SMILES: O=S(=O)(c1ccc(F)cc1)N1c2ccc(C(O)(C(F)(F)F)C(F)(F)F)cc2CC[C@H]1Cc1nnc(-c2ccncc2)o1]

To a solution of (S)—N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)isonicotinohydrazide, TFA (Ex. 11, 13 mg, 0.017 mmol) in DCM (1 mL) was added DIEA (0.012 mL, 0.069 mmol), and Ts-Cl (9.93 mg, 0.052 mmol). The resulting mixture was stirred at rt for 60 hrs. To the reaction mixture was added MeOH (1 ml), the contents concentrated under reduced pressure and purified by preparative HPLC (condition C) to afford the title compound as TFA salt (8.0 mg, 0.0011 mmol, 63% yield). LC/MS (M+1): 617.3; $^1$H-NMR (500 MHz, DMSO-$d_6$) δ ppm 9.04-8.81 (m, 2H), 7.95-7.83 (m, 2H), 7.70 (d, J=8.4 Hz, 1H), 7.65-7.49 (m, 3H), 7.43 (s, 1H), 7.38-7.17 (m, 2H), 4.94-4.60 (m, 1H), 3.29 (m, 1H), 3.14 (m, 1H), 2.82-2.64 (m, 1H), 2.20-1.89 (m, 2H), 1.85-1.31 (m, 1H).

Example 14

2-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol

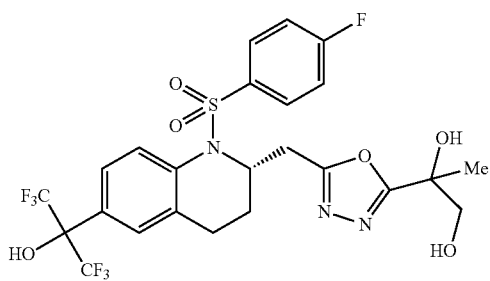 [SMILES: CC(O)(CO)c1nnc(C[C@@H]2CCc3cc(C(O)(C(F)(F)F)C(F)(F)F)ccc3N2S(=O)(=O)c2ccc(F)cc2)o1]

Step A: (S)-1,1,1,3,3,3-hexafluoro-2-(1-((4-fluorophenyl)sulfonyl)-2-((5-(prop-1-en-2-yl)-1,3,4-oxadiazol-2-yl)methyl)-1,2,3,4-tetrahydroquinolin-6-yl)propan-2-ol

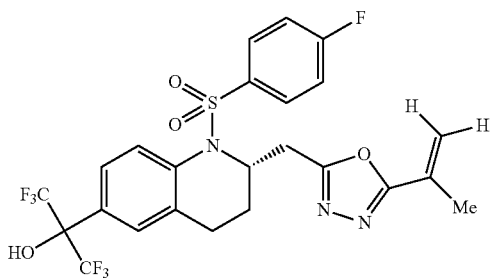 [SMILES: C=C(C)c1nnc(C[C@@H]2CCc3cc(C(O)(C(F)(F)F)C(F)(F)F)ccc3N2S(=O)(=O)c2ccc(F)cc2)o1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (Ex. 8, step A, 20 mg, 0.038 mmol) was treated with methacrylic acid (4.88 mg, 0.057 mmol) to provide the coupling product as crude material (30 mg). It was dissolved in DCM (1 mL), DIEA (0.020 ml, 0.113 mmol) and Ts-Cl (21.61 mg, 0.113 mmol) were added. The resultant mixture was stirred at rt for 15 hrs. It was diluted with ethyl acetate (60 ml), washed with saturated NaHCO$_3$, water, brine, dried (MgSO$_4$) and concentrated under reduced pressure. The residue was purified by flash silica gel chromatography using a 30% mixture of ethyl acetate in hexane to provide (S)-1,1,1,3,3,3-hexafluoro-2-(1-((4-fluorophenyl)sulfonyl)-2-((5-(prop-1-en-2-yl)-1,3,4-oxadiazol-2-yl)methyl)-1,2,3,4-tetrahydroquinolin-6-yl)propan-2-ol (16 mg, 0.028 mmol, 73% yield). LC/MS (M+1): 580.2.

Step B: 2-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol

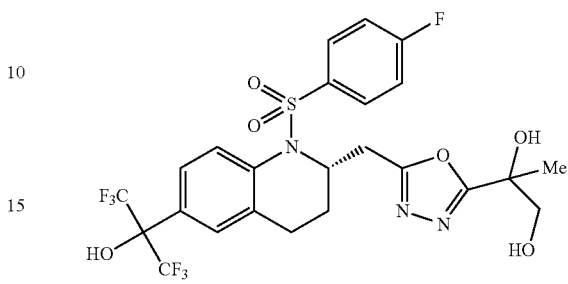

NMO (4.47 mg, 0.038 mmol) and osmium tetroxide (9.21 μl, 1.467 μmol) were added to the solution of (S)-1,1,1,3,3,3-hexafluoro-2-(1-((4-fluorophenyl)sulfonyl)-2-((5-(prop-1-en-2-yl)-1,3,4-oxadiazol-2-yl)methyl)-1,2,3,4-tetrahydroquinolin-6-yl)propan-2-ol (16 mg, 0.028 mmol) in acetone (0.4 ml), water (0.1 mL), THF (0.2 mL) and t-butanol (0.2 mL) at 0° C. The resultant mixture was warmed up to rt for 15 hrs. and concentrated under reduced pressure. The residue was purified by preparative HPLC to provide the title compound (15 mg, 0.024 mmol, 81% yield) as a mixture of diastereomers which was separated into its homochiral components using a chiral AD column to provide diastereomer A as first eluent off the column (2.8 mg). LC/MS (M+1): 614.2. $^1$H-NMR (400 MHz, CD$_3$OD) δ ppm 7.77 (d, J=8.8 Hz, 1H), 7.69-7.59 (m, 1H), 7.59-7.49 (m, 2H), 7.44 (s, 1H), 7.27-7.07 (m, 2H), 4.81-4.69 (m, 1H), 3.98-3.86 (m, 1H), 3.24-3.13 (m, 2H), 2.60-2.46 (m, 1H), 2.04 (m, 1H), 1.92-1.81 (m, 1H), 1.74-1.64 (m, 1H), 1.62-1.51 (m, 3H), 1.40-1.29 (m, 1H). Diastereomer B as second eluent off the column (2.6 mg). LC/MS (M+1): 614.2. $^1$H-NMR (400 MHz, CD$_3$OD) δ ppm 7.78 (d, J=8.6 Hz, 1H), 7.89-7.67 (m, 1H), 7.68-7.60 (m, 1H), 7.60-7.49 (m, 2H), 7.44 (s, 1H), 7.29-7.00 (m, 2H), 4.79-4.70 (m, 1H), 4.33-4.19 (m, 1H), 3.86-3.67 (m, 2H), 3.27-3.07 (m, 2H), 2.56 (m, 1H), 2.05 (m, 1H), 1.92-1.76 (m, 1H), 1.67-1.55 (m, 3H).

Example 15

1-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)butan-2-ol

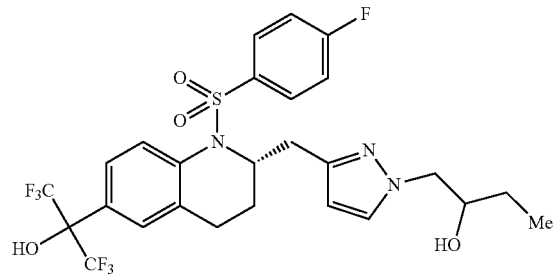 [SMILES: CCC(O)Cn1ccc(C[C@@H]2CCc3cc(C(O)(C(F)(F)F)C(F)(F)F)ccc3N2S(=O)(=O)c2ccc(F)cc2)n1]

Step A: (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)but-3-yn-2-one

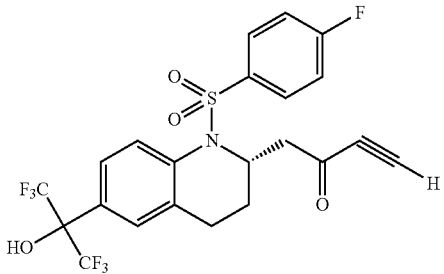 [SMILES: C#CC(=O)C[C@@H]1CCc2cc(C(O)(C(F)(F)F)C(F)(F)F)ccc2N1S(=O)(=O)c1ccc(F)cc1]

To a solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (130 mg, 0.252 mmol) in DMF (1 mL) were added DIEA (0.132 mL, 0.757 mmol), BOP (134 mg, 0.303 mmol) and N,O-dimethylhydroxylamine, HCl (29.5 mg, 0.303 mmol). The resulting mixture was stirred at rt for 1 h. It was diluted with ethyl acetate (60 ml), washed with water, brine, dried (MgSO$_4$) and concentrated under reduced pressure. The residue was dissolved in THF (2 mL) and cooled to 0° C. To this was added 0.5 M ether solution of ethynylmagnesium bromide (2.52 mL, 1.26 mmol). The resultant mixture was warmed to over 1 hr. and quenched with saturated NH$_4$Cl (2 ml). The reaction mixture was diluted with ethyl acetate (60 ml), washed with water, brine, dried (MgSO$_4$) and concentrated by vacuum. The residue was purified by flash silica gel chromatography using a 25% mixture of ethyl acetate in hexane to provide (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)but-3-yn-2-one (98 mg, 0.187 mmol, 74% yield). $^1$H-NMR (400 MHz, CDCl$_3$) δ ppm 7.81 (d, J=8.8 Hz, 1H), 7.60 (d, J=8.6 Hz, 1H), 7.55-7.42 (m, 2H), 7.37 (s, 1H), 7.18-6.97 (m, 2H), 4.79-4.64 (m, 1H), 3.91 (s, 1H), 3.21 (m, 1H), 2.86 (m, 1H), 2.56-2.39 (m, 1H), 2.16-2.00 (m, 1H), 1.87-1.78 (m, 1H), 1.54-1.37 (m, 1H).

Step B: 1-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)butan-2-ol

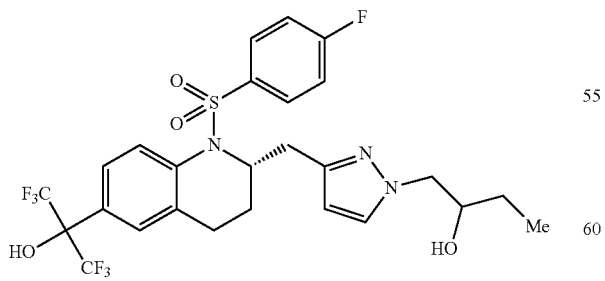

To a solution of (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)but-3-yn-2-one (25 mg, 0.048 mmol) in MeOH (1 mL) was added 1-hydrazinylbutan-2-ol (14.9 mg, 0.143 mmol). The resulting mixture was stirred at rt for 1 hr and concentrated under reduced pressure. The residue was purified by flash silica gel chromatography using a 40% mixture of ethyl acetate in hexane to provide the title compound (4.0 mg, 0.0066 mmol, 14% yield). LC/MS (M+1): 610.2; $^1$H-NMR (400 MHz, CD$_3$OD) δ ppm 7.81-7.64 (m, 2H), 7.64-7.49 (m, 3H), 7.49-7.35 (m, 1H), 7.24-6.97 (m, 2H), 6.22-6.12 (m, 1H), 4.69-4.55 (m, 1H), 4.11-4.05 (m, 1H), 4.03-3.91 (m, 1H), 3.91-3.72 (m, 1H), 3.02-2.94 (m, 1H), 2.88-2.78 (m, 1H), 2.73-2.55 (m, 1H), 1.94-1.73 (m, 2H), 1.66-1.34 (m, 3H), 1.07-0.94 (m, 3H).

Example 16

(S)-1,1,1,3,3,3-hexafluoro-2-(2-((1-((4-fluorobenzyl)-1H-pyrazol-5-yl)methyl)-1-((4-fluorophenyl)sulfonyl)-1,2,3,4-tetrahydroquinolin-6-yl)propan-2-ol

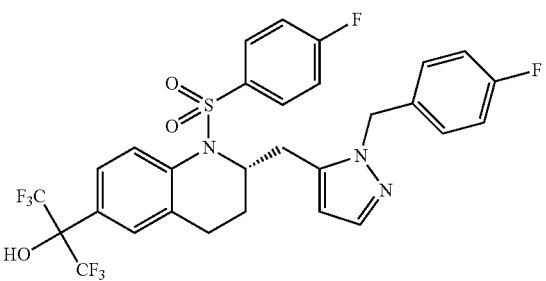 [SMILES: O=S(=O)(c1ccc(F)cc1)N1c2ccc(C(O)(C(F)(F)F)C(F)(F)F)cc2CC[C@H]1Cc1ccnn1Cc1ccc(F)cc1]

Following similar procedure as in Step B of Example 15, (S)-1-(1-((4-fluorophenyl)sulfonyl)-6-(1,1,1,3,3,3-hexafluoro-2-hydroxypropan-2-yl)-1,2,3,4-tetrahydroquinolin-2-yl)but-3-yn-2-one (20 mg, 0.038 mmol) was treated with (4-fluorobenzyl)hydrazine (24.4 mg, 0.115 mmol) to provide the title compound (20 mg, 0.013 mmol, 35% yield). LC/MS (M+1): 646.3; $^1$H-NMR (500 MHz, DMSO-d$_6$) δ ppm 8.75 (m, 1H), 7.72-7.66 (m, 1H), 7.62-7.49 (m, 2H), 7.49-7.27 (m, 5H), 7.27-7.12 (m, 3H), 7.03 (m, 1H), 6.27-6.03 (m, 1H), 5.32-5.20 (m, 2H), 4.62-4.35 (m, 1H), 3.52-3.42 (m, 1H), 2.83-2.53 (m, 2H), 1.93-1.80 (m, 1H), 1.74-1.60 (m, 1H), 1.60-1.41 (m, 1H).

Example 17

3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol

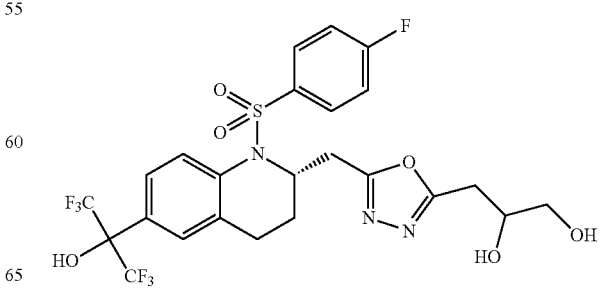

Step A: (S)-2-(2-((5-allyl-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol

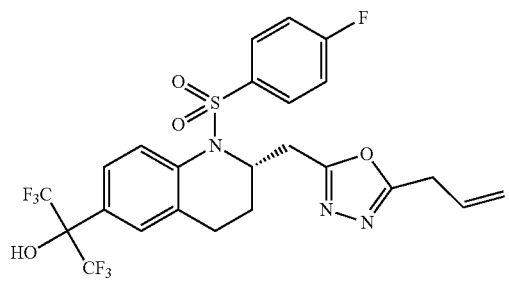 [SMILES: C=CCc1nnc(C[C@@H]2CCc3cc(C(O)(C(F)(F)F)C(F)(F)F)ccc3N2S(=O)(=O)c2ccc(F)cc2)o1]

Following similar procedure as in Step B of Example 1, (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (Ex. 8, step A, 90 mg, 0.170 mmol) was treated with but-3-enoic acid (21.95 mg, 0.255 mmol) to provide the coupled product (110 mg). This was dissolved in DCM (2 mL), DIEA (0.089 ml, 0.51 mmol) and Ts-Cl (97 mg, 0.51 mmol) were added. The resultanting mixture was stirred at rt for 72 hrs diluted with ethyl acetate (60 ml), washed with satuarated NaHCO₃, water, brine, dried (MgSO₄) and concentrated under vacuum. The residue was purified by flash silica gel chromatography using a mixture of 30% ethyl acetate in hexane to provide (S)-2-(2-((5-allyl-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol (40 mg). LCMS indicated that it's ~50% purity. It was directly converted to the next step without further purification. LC/MS (M+1): 580.2

Step B: 3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol

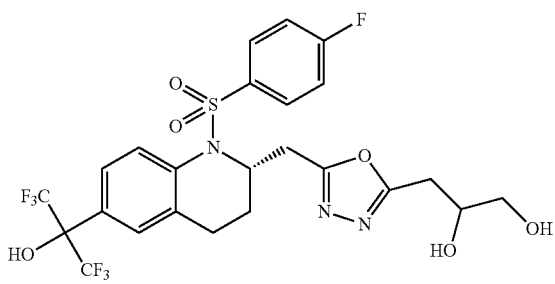 [SMILES: O=S(=O)(c1ccc(F)cc1)N1c2ccc(C(O)(C(F)(F)F)C(F)(F)F)cc2CC[C@H]1Cc1nnc(CC(O)CO)o1]

Following similar procedure as in Step B of Example 16, (S)-2-(2-((5-allyl-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol (40 mg, 0.069 mmol) was converted to the title compound (18 mg, 0.028 mmol, 40% yield) as a mixture of diastereomers. LC/MS (M+1): 614.2. ¹H-NMR (400 MHz, CD₃OD) δ ppm 7.77 (d, J=8.6 Hz, 1H), 7.62 (d, J=8.8 Hz, 1H), 7.60-7.49 (m, 2H), 7.44 (s, 1H), 7.28-7.13 (m, 2H), 4.78-4.68 (m, 1H), 4.24-4.05 (m, 1H), 3.87-3.67 (m, 1H), 3.67-3.53 (m, 2H), 3.22-3.07 (m, 3H), 3.05-2.88 (m, 1H), 2.56 (m, 1H), 2.12-2.00 (m, 1H), 1.90-1.81 (m, 1H), 1.72-1.50 (m, 1H).

Example 18

3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol

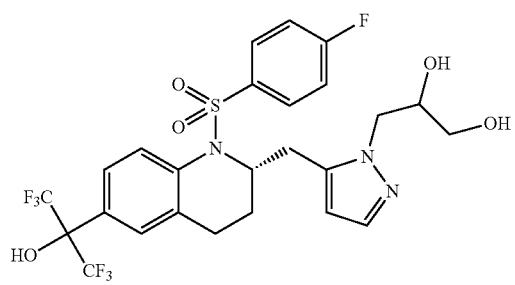 [SMILES: O=S(=O)(c1ccc(F)cc1)N1c2ccc(C(O)(C(F)(F)F)C(F)(F)F)cc2CC[C@H]1Cc1ccnn1CC(O)CO]

Step A: (S)-2-(2-((1-allyl-1H-pyrazol-5-yl)methyl)-1-((4-fluorophenyl)sulfonyl)-1,2,3,4-tetrahydroquinolin-6-yl)-1,1,1,3,3,3-hexafluoropropan-2-ol & (S)-2-(2-((1-allyl-1H-pyrazol-3-yl)methyl)-1-((4-fluorophenyl)sulfonyl)-1,2,3,4-tetrahydroquinolin-6-yl)-1,1,1,3,3,3-hexafluoropropan-2-ol

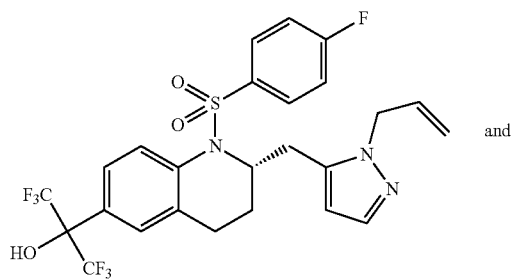

and

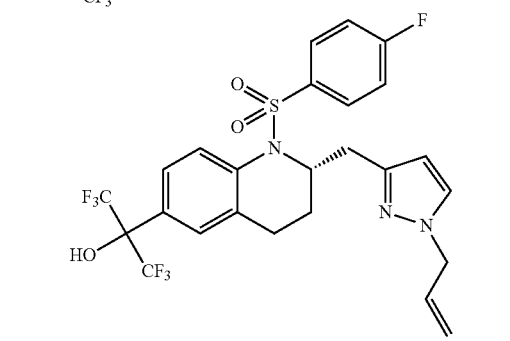

To a solution of (S)-1-(1-((4-fluorophenyl)sulfonyl)-6-(1,1,3,3,3-hexafluoro-2-hydroxypropan-2-yl)-1,2,3,4-tetrahydroquinolin-2-yl)but-3-yn-2-one (Ex. 15, step A, 60 mg, 0.115 mmol) in MeOH (1 mL) was added allyl hydrazine (41.3 mg, 0.573 mmol). The resulting mixture was stirred at rt for 1 hr. and purified by fresh silica gel chromatography followed by chrial AD column to provide (S)-2-(2-((1-allyl-1H-pyrazol-5-yl)methyl)-1-((4-fluorophenyl)sulfonyl)-1,2,3,4-tetrahydroquinolin-6-yl)-1,1,1,3,3,3-hexafluoropropan- 2-ol as first eluent off the column (14 mg, 0.024 mmol, 21% yield). LC/MS (M+1): 578.3; ¹H-NMR (400 MHz, CD₃OD) δ ppm 7.74 (d, J=8.8 Hz, 1H), 7.66-7.48 (m, 3H), 7.48-7.32 (m, 2H), 7.31-7.12 (m, 2H), 6.35-6.15 (m, 1H), 6.08-5.86 (m, 1H), 5.30-5.10 (m, 1H), 4.99-4.87 (m, 1H), 4.79-4.70 (m, 1H), 4.64-4.45 (m, 2H), 3.16-2.86 (m, 2H), 2.66-2.39 (m, 1H), 2.09-1.82 (m, 2H), 1.65-1.48 (m, 1H) and (S)-2-(2-((1-allyl-1H-pyrazol-3-yl)methyl)-1-((4-fluorophenyl)sulfonyl)-1,2,3,4-tetrahydroquinolin-6-yl)-1,1,1,3,3,3-hexafluoropropan-2-ol as second eluent off the column (14 mg, 0.024 mmol, 21% yield). LC/MS (M+1): 578.3; ¹H-NMR (400 MHz, CD₃OD) δ ppm 7.74 (d, J=8.8 Hz, 1H), 7.67-7.46 (m, 4H), 7.46-7.34 (m, 1H), 7.26-7.06 (m, 2H), 6.30-6.13 (m, 1H), 6.10-5.82 (m, 1H), 5.30-4.96 (m, 2H), 4.92-4.87 (m, 1H), 4.73-4.63 (m, 2H), 3.10-2.76 (m, 2H), 2.59 (ddd, J=16.3, 8.0, 5.8 Hz, 1H), 2.09-1.93 (m, 1H), 1.79 (ddt, J=13.7, 8.0, 5.7 Hz, 1H), 1.67-1.50 (m, 1H).

Step B: 3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol

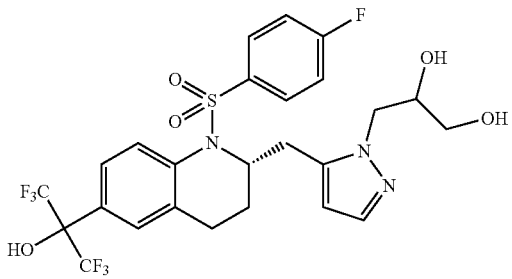

Following similar procedure as in Step B of Example 16, (S)-2-(2-((1-allyl-1H-pyrazol-5-yl)methyl)-1-((4-fluorophenyl)sulfonyl)-1,2,3,4-tetrahydroquinolin-6-yl)-1,1,1,3,3,3-hexafluoropropan-2-ol (14 mg, 0.024 mmol) was converted to the title compound (7.1 mg, 0.011 mmol, 47% yield). LC/MS (M+1): 612.1. ¹H-NMR (500 MHz, DMSO-d₆) δ ppm 8.94-8.60 (m, 1H), 7.81-7.65 (m, 1H), 7.70-7.49 (m, 3H), 7.40 (d, J=9.4 Hz, 1H), 7.38-7.28 (m, 3H), 6.25-5.82 (m, 1H), 5.13-4.82 (m, 1H), 4.69-4.53 (m, 1H), 4.19-3.95 (m, 1H), 3.98-3.61 (m, 1H), 3.31-3.22 (m, 1H), 3.10-2.89 (m, 2H), 2.69-2.53 (m, 2H), 2.09-1.91 (m, 1H), 1.87-1.65 (m, 2H), 1.57-1.40 (m, 1H).

Example 19

3-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol

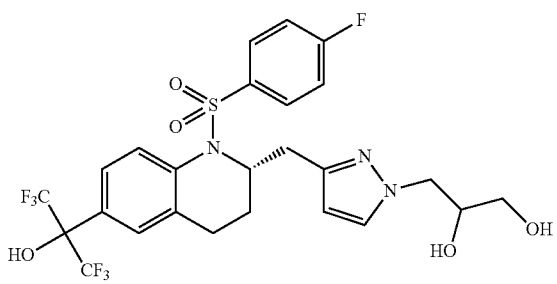 [SMILES: O=S(=O)(c1ccc(F)cc1)N1c2ccc(C(O)(C(F)(F)F)C(F)(F)F)cc2CC[C@H]1Cc1ccn(CC(O)CO)n1]

Following similar procedure as in Step B of Example 14, (S)-2-(2-((1-allyl-1H-pyrazol-3-yl)methyl)-1-((4-fluorophenyl)sulfonyl)-1,2,3,4-tetrahydroquinolin-6-yl)-1,1,1,3,3,3-hexafluoropropan-2-ol (e.g. 68, step A, second eluent, 14 mg, 0.024 mmol) was converted to the title compound (2.0 mg, 0.003 mmol, 13% yield). LC/MS (M+1): 612.1. ¹H-NMR (500 MHz, DMSO-d₆) δ ppm 8.89-8.59 (m, 1H), 7.78-7.66 (m, 1H), 7.66-7.58 (m, 2H), 7.58-7.49 (m, 2H), 7.46-7.26 (m, 3H), 6.11-5.98 (m, 1H), 4.91 (m, 1H), 4.71 (m, 1H), 4.57 (m, 1H), 4.11 (m, 1H), 3.97-3.83 (m, 1H), 3.80-3.70 (m, 1H), 3.33-3.22 (m, 1H), 2.83-2.62 (m, 1H), 2.14 (m, 1H), 1.63-1.60 (m, 2H), 1.59-1.39 (m, 1H).

Example 20

(S)-benzyl 2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetate

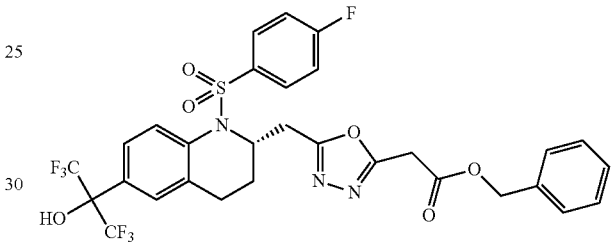

BOP (37.6 mg, 0.085 mmol) was added to the solution of (S)-2-(1-((4-fluorophenyl)sulfonyl)-6-(1,1,1,3,3,3-hexafluoro-2-hydroxypropan-2-yl)-1,2,3,4-tetrahydroquinolin-2-yl)acetohydrazide (example 8, step A, 30 mg, 0.057 mmol), DIEA (0.030 ml, 0.170 mmol) and 3-(benzyloxy)-3-oxopropanoic acid (16.51 mg, 0.085 mmol) in DMF (1 ml) at rt and stirred for 1 hr. The reaction mixture was extracted with ethyl acetate (60 ml), washed with saturated aq. NaHCO₃, water, brine, dried (MgSO₄) and concentrated under vacuum. The residue was dissolved in DCM (1 ml), DIEA (0.030 ml, 0.170 mmol) and Ts-Cl (32.4 mg, 0.170 mmol) were added and the contents stirred at rt for 72 hrs. The reaction mixture was extracted with ethyl acetate (60 ml). washed with saturated aq. NaHCO₃, water, brine, dried (MgSO₄) and concentrated under vacuum. The residue was purified by flash silica gel chromatography using a mixture of 30% ethyl acetate in hexane to provide the title compound (20 mg, 0.026 mmol, 46% yield). LC/MS (M+1): 688.3; ¹H-NMR (400 MHz, CD₃OD) δ ppm 7.79-7.70 (m, 1H), 7.63-7.48 (m, 3H), 7.47-7.25 (m, 6H), 7.24-7.11 (m, 2H), 5.32-5.15 (m, 2H), 4.80-4.66 (m, 1H), 3.25-3.10 (m, 2H), 2.60-2.47 (m, 1H), 2.00 (m, 1H), 1.91-1.77 (m, 1H), 1.67-1.52 (m, 1H).

Example 21

(S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)-N,N-dimethylacetamide

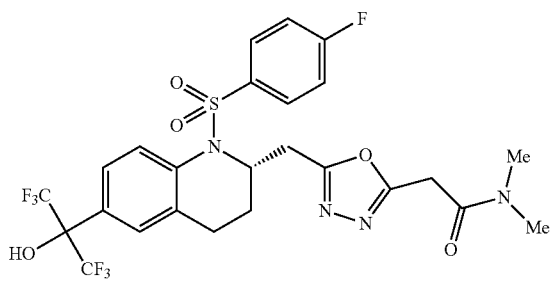 [SMILES: CN(C)C(=O)Cc1nnc(C[C@@H]2CCc3cc(C(O)(C(F)(F)F)C(F)(F)F)ccc3N2S(=O)(=O)c2ccc(F)cc2)o1]

Step A: (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetic acid

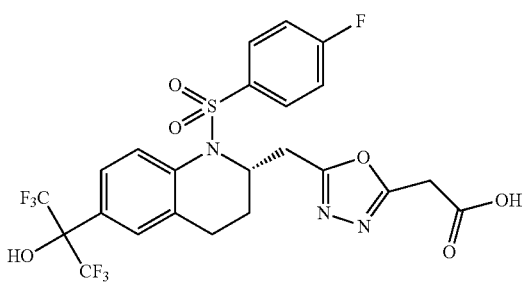 [SMILES: O=C(O)Cc1nnc(C[C@@H]2CCc3cc(C(O)(C(F)(F)F)C(F)(F)F)ccc3N2S(=O)(=O)c2ccc(F)cc2)o1]

To a solution of (S)-benzyl 2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetate (example 20, 18 mg, 0.026 mmol) in MeOH (5 mL) was added 5% palladium on carbon (5.6 mg, 2.62 μmol) and the contents stirred under H$_2$ atmosphere at 20 Psi at rt for 1 hr. and filtered. The filtrate was concentrated under vacuum to provide (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetic acid (15 mg, 0.023 mmol, 86% yield). LC/MS (M+1): 598.1; $^1$H-NMR (400 MHz, CD$_3$OD) δ ppm 7.86-7.71 (m, 1H), 7.68-7.50 (m, 3H), 7.43 (s, 1H), 7.23-7.08 (m, 2H), 4.80-4.69 (m, 1H), 4.20-4.10 (m, 1H), 3.89-3.72 (m, 1H), 3.26-3.07 (m, 2H), 2.67-2.48 (m, 1H), 2.11-2.02 (m, 1H), 1.94-1.82 (m, 1H), 1.77-1.55 (m, 1H).

Step B: (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)-N,N-dimethylacetamide

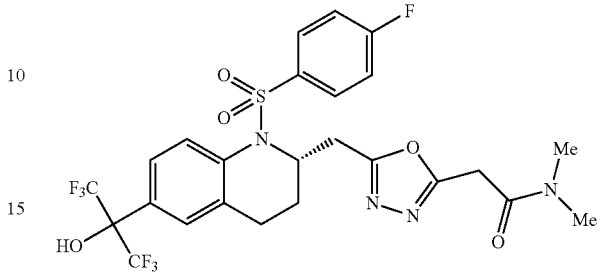

Following similar procedure as in Step B of Example 1, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetic acid (10 mg, 0.017 mmol) was treated with dimethylamine (0.033 ml, 0.067 mmol) to provide the title compound (4.8 mg, 0.007 mmol, 45% yield). LC/MS (M+1): 625.2; $^1$H-NMR (500 MHz, 1 to 1 mixture of CDCl3 and CD3OD) δ ppm 7.76 (d, J=8.4 Hz, 1H), 7.63 (d, J=8.9 Hz, 1H), 7.53-7.37 (m, 3H), 7.20-7.06 (m, 2H), 4.87-4.74 (m, 1H), 3.25-3.10 (m, 5H), 3.02 (s, 3H), 2.53 (m, 1H), 2.02 (m, 1H), 1.85-1.78 (m, 1H), 1.71-1.54 (m, 1H).

Example 22

(S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetamide

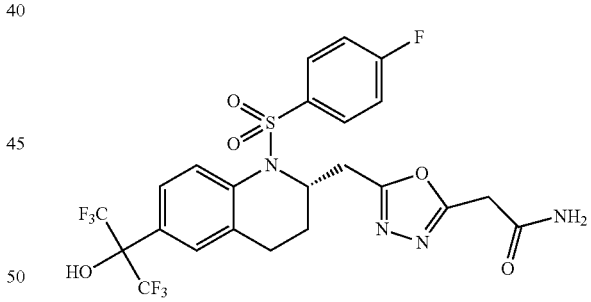

Following similar procedure as in Step B of Example 1, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetic acid (example 21, step A, 12 mg, 0.020 mmol) was treated with 7.0 M MeOH solution of ammonia (0.017 ml, 0.121 mmol) to provide the title compound (6.6 mg, 0.011 mmol, 55% yield). LC/MS (M+1): 597.1; $^1$H-NMR (500 MHz, DMSO-d$_6$) δ ppm 8.75 (br. s., 1H), 7.81-7.63 (m, 2H), 7.63-7.48 (m, 3H), 7.46-7.23 (m, 4H), 4.77-4.52 (m, 1H), 4.00-3.65 (m, 2H), 3.19-3.01 (m, 2H), 2.66-2.59 (m, 1H), 2.11-1.85 (m, 2H), 1.69-1.54 (m, 1H).

The Examples in TABLE 1 below were prepared in the same manner as outlined in examples above, substituting the appropriate amine

TABLE 1

| Ex. No. | Structure | MW | HPLC ret. time (min.) | HPLC method | MS (M$^{+1}$) |
|---|---|---|---|---|---|
| 23 | 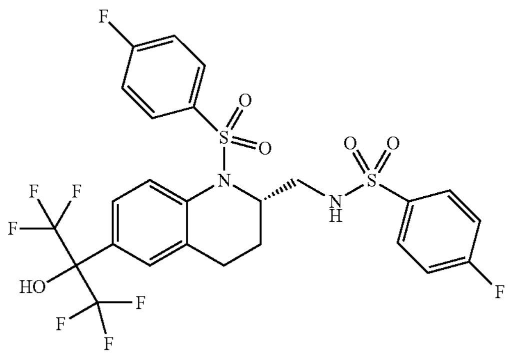 [SMILES: O=S(=O)(NC[C@@H]1CCc2cc(C(O)(C(F)(F)F)C(F)(F)F)ccc2N1S(=O)(=O)c1ccc(F)cc1)c1ccc(F)cc1] | 644.6 | 2.07 | G | 645.3 |
| 24 | 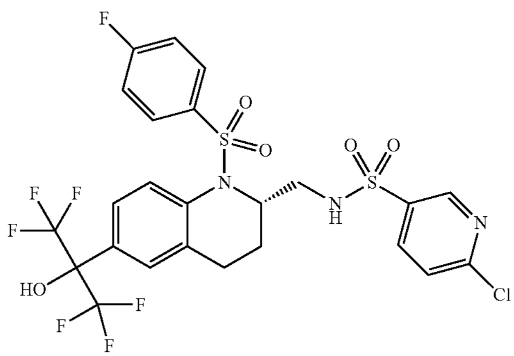 [SMILES: O=S(=O)(NC[C@@H]1CCc2cc(C(O)(C(F)(F)F)C(F)(F)F)ccc2N1S(=O)(=O)c1ccc(F)cc1)c1ccc(Cl)nc1] | 662 | 2.04 | G | 662.2 |
| 25 | 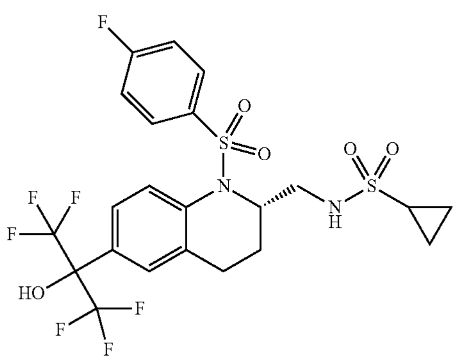 [SMILES: O=S(=O)(NC[C@@H]1CCc2cc(C(O)(C(F)(F)F)C(F)(F)F)ccc2N1S(=O)(=O)c1ccc(F)cc1)C1CC1] | 590.5 | 1.89 | G | 591.2 |
| 26 | 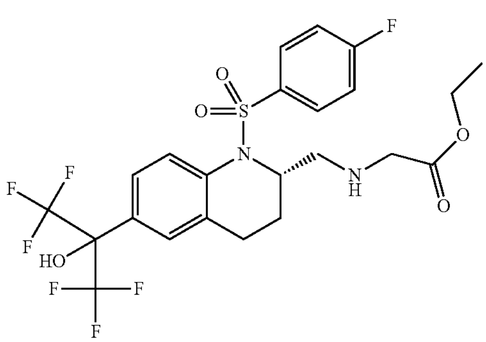 [SMILES: CCOC(=O)CNC[C@@H]1CCc2cc(C(O)(C(F)(F)F)C(F)(F)F)ccc2N1S(=O)(=O)c1ccc(F)cc1] | 572.5 | 3.54 | F | 573.4 |

TABLE 1-continued

| Ex. No. | Structure | MW | HPLC ret. time (min.) | HPLC method | MS (M+1) |
|---|---|---|---|---|---|
| 27 | 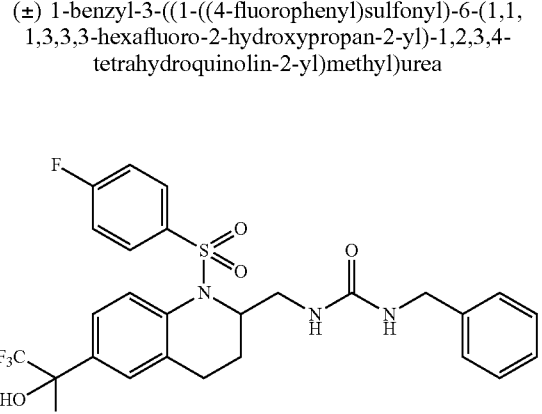 | 576.5 | 1.98 | G | 577.2 |

Example 28

(±) 1-cyclopropyl-3-((1-((4-fluorophenyl)sulfonyl)-6-(1,1,1,3,3,3-hexafluoro-2-hydroxypropan-2-yl)-1,2,3,4-tetrahydroquinolin-2-yl)methyl)urea

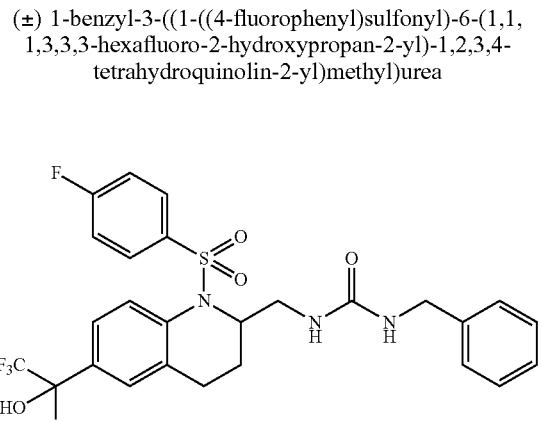

A mixture of 2-(1-((4-fluorophenyl)sulfonyl)-6-(1,1,1,3,3,3-hexafluoro-2-hydroxypropan-2-yl)-1,2,3,4-tetrahydroquinolin-2-yl)acetic acid (20 mg, 0.039 mmol) in toluene (1 mL) was added triethylamine (0.027 mL, 0.194 mmol) and diphenylphosphoryl azide (21.36 mg, 0.078 mmol). The resultant solution was refluxed at 100° C. for 30 min. After addition of cyclopropylamine (5.32 mg, 0.093 mmol) at room temperature, the reaction was refluxed at 100° C. for another 5 h, cooled to rt and purified via preparative HPLC (condition B). The product had an HPLC ret. time=3.24 min.–Column: (condition A); LC/MS M+1=570.1. $^1$H NMR (500 MHz, METHANOL-d$_4$) δ 7.79 (d, J=8.9 Hz, 1H), 7.61 (d, J=8.9 Hz, 1H), 7.52-7.47 (m, 2H), 7.40 (s, 1H), 7.15-7.07 (m, 2H), 4.44 (d, J=2.5 Hz, 1H), 3.38 (dd, J=13.9, 5.0 Hz, 1H), 3.16 (dd, J=13.9, 7.9 Hz, 1H), 2.52-2.40 (m, 2H), 1.95-1.85 (m, 1H), 1.73 (s, 1H), 1.56-1.45 (m, 1H), 0.77-0.67 (m, 2H), 0.58-0.44 (m, 2H).

Example 29

(±) 1-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-3-phenylurea

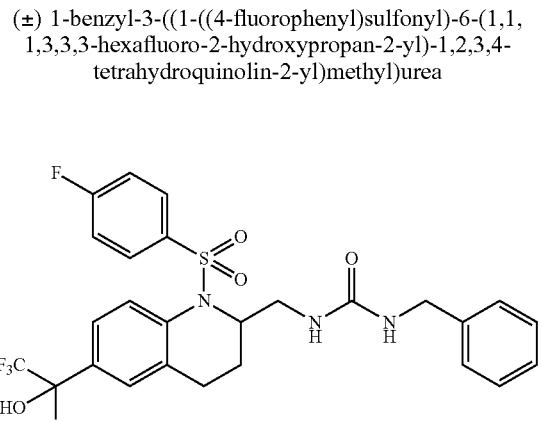

The compound was prepared in the same manner as in example 408 above, substituting cyclopropylamine with aniline. The yield of the product was 9.1 mg (36.8% yield and the product had an HPLC ret. time=3.40 min.–Column: (condition A); LC/MS M+1=606.1. $^1$H NMR (500 MHz, METHANOL-d$_4$) δ 7.79 (d, J=8.4 Hz, 1H), 7.62 (d, J=8.9 Hz, 1H), 7.52-7.46 (m, 2H), 7.41 (s, 1H), 7.34 (d, J=7.4 Hz, 2H), 7.25 (t, J=7.9 Hz, 2H), 7.09 (t, J=8.7 Hz, 2H), 6.99 (t, J=7.4 Hz, 1H), 4.45 (d, J=2.0 Hz, 1H), 3.44 (dd, J=14.1, 5.2 Hz, 1H), 3.18 (dd, J=14.1, 7.7 Hz, 1H), 2.59-2.43 (m, 1H), 1.92 (s, 1H), 1.84-1.74 (m, 1H), 1.61-1.47 (m, 1H).

Example 30

(±) 1-benzyl-3-((1-((4-fluorophenyl)sulfonyl)-6-(1,1,1,3,3,3-hexafluoro-2-hydroxypropan-2-yl)-1,2,3,4-tetrahydroquinolin-2-yl)methyl)urea

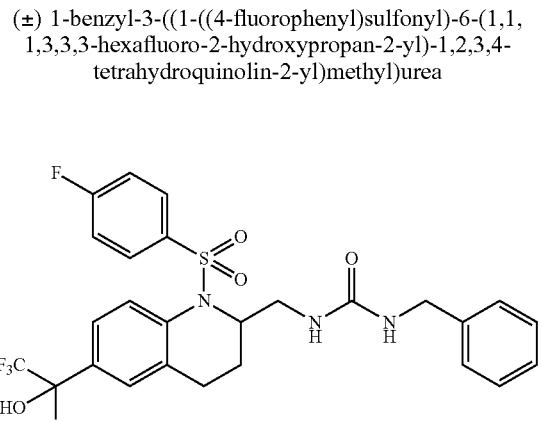

The compound was prepared in the same manner as in example 408 above, substituting cyclopropylamine with benzylamine. The yield of the product was 19.9 mg (83.0% yield) and the product had an HPLC ret. time=3.42 min.–Column: (condition A); LC/MS M+1=620.2. $^1$H NMR (500 MHz, METHANOL-$d_4$) δ 7.78-7.74 (m, 1H), 7.61 (s, 2H), 7.51-7.46 (m, 2H), 7.40 (s, 1H), 7.31-7.30 (m, 2H), 7.25-7.20 (m, 1H), 7.12-7.07 (m, 2H), 4.43-4.36 (m, 1H), 4.33 (s, 2H), 3.40-3.35 (m, 1H), 3.14 (dd, J=13.9, 7.4 Hz, 1H), 2.49 (dt, J=15.9, 6.2 Hz, 1H), 1.86 (dt, J=13.1, 6.3 Hz, 1H), 1.82-1.72 (m, 1H), 1.56-1.46 (m, 1H).

General RORγ SPA Binding Assay

The binding of potential ligands to RORγ is measured by competition with [$^3$H] 25-hydroxycholesterol using a scintillation proximity assay (SPA) binding assay. The ligand binding domain of human RORγ (A262-5507) with an N-terminal His tag is expressed in *E. coli* and purified using nickel affinity chromotography. 50 nM RORγ (A262-5507) is incubated with test compound at varying concentrations for 15 min at room temperature in PBS buffer containing 0.5% fatty acid free BSA. 10 nM of [$^3$H] 25-hydroxycholesterol is then added, and the reaction is incubated for 15 min. 4 mg/mL of Ysi Copper HIS-TAG SPA Beads (Perkin Elmer) are added, and the mixture is incubated for 30 min. The reaction is read on a MicroBeta Trilux scintillation plate reader (Perkin Elmer). $IC_{50}$ values are determined from the percentage inhibition of [$^3$H] 25-hydroxycholesterol binding.

$IC_{50}$ values of the compounds of the invention in the RORγ binding assay are provided below.

| Example # | RORgt Binding IC50, nM |
| --- | --- |
| 1 | 24 |
| 2 | 21 |
| 3 | 493 |
| 4 | 718 |
| 5 | 342 |
| 6 | 109 |
| 7 | 172 |
| 8 | 43 |
| 9 | 45 |
| 10 | 155 |
| 11 | 60 |
| 12 | 131 |
| 13 | 27 |
| 14A | 23 |
| 14B | 20 |
| 15 | 54 |
| 16 | 192 |
| 17 | 13 |
| 18 | 14 |
| 19 | 16 |
| 20 | 122 |
| 21 | 93 |
| 22 | 34 |
| 23 | 150 |
| 24 | 220 |
| 25 | 200 |
| 26 | 150 |
| 27 | 280 |
| 28 | 155 |
| 29 | 308 |
| 30 | 160 |

We claim:

1. A compound which is
(S)—N'-(2-(1-((4-fluorophenyl)sulfonyl)-6-(1,1,1,3,3,3-hexafluoro-2-hydroxypropan-2-yl)-1,2,3,4-tetrahydroquinolin-2-yl)acetyl)-2-hydroxy-2-methylpropanehydrazide,
(S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetonitrile,
(S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-phenyl oxime,
(S,E)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime,
(S,Z)-1-(1-((4-fluorophenyl)sulfonyl)-6-(1,1,1,3,3,3-hexafluoro-2-hydroxypropan-2-yl)-1,2,3,4-tetrahydroquinolin-2-yl)propan-2-one O-ethyl oxime,
(S)-1,1,1,3,3,3-hexafluoro-2-(1-((4-fluorophenyl)sulfonyl)-2-((5-(methylthio)-1,3,4-thiadiazol-2-yl)methyl)-1,2,3,4-tetrahydroquinolin-6-yl)propan-2-ol,
(S)-1,1,1,3,3,3-hexafluoro-2-(1-((4-fluorophenyl)sulfonyl)-2-((5-(methylsulfonyl)-1,3,4-thiadiazol-2-yl)methyl)-1,2,3,4-tetrahydroquinolin-6-yl)propan-2-ol,
(S)-1,1,1,3,3,3-hexafluoro-2-(1-((4-fluorophenyl)sulfonyl)-2-((5-(2-hydroxypropan-2-yl)-1,3,4-oxadiazol-2-yl)methyl)-1,2,3,4-tetrahydroquinolin-6-yl)propan-2-ol,
(S)-2-(2-((5-(2-amino-2-methylpropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol,
(S)-3-amino-N'-(2-(1-((4-fluorophenyl)sulfonyl)-6-(1,1,3,3,3-hexafluoro-2-hydroxypropan-2-yl)-1,2,3,4-tetrahydroquinolin-2-yl)acetyl)-3-methylbutanehydrazide,
(S)—N'-(2-(1-((4-fluorophenyl)sulfonyl)-6-(1, 1,1,3,3,3-hexafluoro-2-hydroxypropan-2-yl)-1,2,3,4-tetrahydroquinolin-2-yl)acetyl)isonicotinohydrazide,
(S)-2-(2-((5-(1-aminocyclopropyl)-1,3,4-oxadiazol-2-yl)methyl)-1-((4-fluorophenyl)sulfonyl)-1,2,3,4-tetrahydroquinolin-6-yl)-1,1,1,3,3,3-hexafluoropropan-2-ol,
(S)-1,1,1,3,3,3-hexafluoro-2-(1-((4-fluorophenyl)sulfonyl)-2-((5-(pyridin-4-yl)-1,3,4-oxadiazol-2-yl)methyl)-1,2,3,4-tetrahydroquinolin-6-yl)propan-2-ol,
2-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol,
1-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-5-yl)butan-2-ol,
(S)-1,1,1,3,3,3-hexafluoro-2-(2-((1-((4-fluorobenzyl)-1H-pyrazol-5-yl)methyl)-1-((4-fluorophenyl)sulfonyl)-1,2,3,4-tetrahydroquinolin-6-yl)propan-2-ol,
3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)propane-1,2-diol,
3-(5-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol,
3-(3-(((S)-1-((4-fluorophenyl)sulfonyl)-6-(1,1,1,3,3,3-hexafluoro-2-hydroxypropan-2-yl)-1,2,3,4-tetrahydroquinolin-2-yl)methyl)-1H-pyrazol-1-yl)propane-1,2-diol,
(S)-benzyl 2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetate, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)-N,N-dimethyl acetamide, (S)-2-(5-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-1,3,4-oxadiazol-2-yl)acetamide, (S)-4-fluoro-N-((1-((4-fluorophenyl)sulfonyl)-6-(1,1,1,3,3,3-hexafluoro-2-hydroxypropan-2-yl)-1,2,3,4-tetrahydroquinolin-2-yl)methyl)benzenesulfonamide, (S)-6-chloro-N-((1-((4-fluorophenyl)sulfonyl)-6-(1,1,1,3,3,3-hexafluoro-2-hydroxypropan-2-yl)-1,2,3,4-tetrahydroquinolin-2-yl)methyl)pyridine-3-sulfonamide, (S)—N-((1-((4-fluorophenyl)sulfonyl)-6-(1,1,1,3,3,3-hexafluoro-2-hydroxypropan-2-yl)-1,2,3,4-tetrahydroquinolin-2-yl)methyl)cyclopropanesulfonamide, (S)-ethyl 2-(((1-((4-fluorophenyl)sulfonyl)-6-(1,1,1,3,3,3-hexafluoro-2-hydroxypropan-2-yl)-1,2,3,4-tetrahydroquinolin-2-yl)methyl)amino)acetate, (S)-2-(2-((benzylamino)methyl)-1-((4-fluorophenyl)sulfonyl)-1,2,3,4-tetrahydroquinolin-6-yl)-1,1,1,3,3,3-hexafluoropropan-2-ol, (±) 1-cyclopropyl-3-((1-((4-fluorophenyl)sulfonyl)-6-(1,1,1,3,3,3-hexafluoro-2-hydroxypropan-2-yl)-1,2,3,4-tetrahydroquinolin-2-yl)methyl)urea, (±) 1-((1-((4-fluorophenyl)sulfonyl)-6-(1,1,1,3,3,3-hexafluoro-2-hydroxypropan-2-yl)-1,2,3,4-tetrahydroquinolin-2-yl)methyl)-3-phenylurea, and (±) 1-benzyl-3-((1-((4-fluorophenyl)sulfonyl)-6-(1,1,1,3,3,3-hexafluoro-2-hydroxypropan-2-yl)-1,2,3,4-tetrahydroquinolin-2-yl)methyl)urea, or a pharmaceutically acceptable salt, stereoisomer or tautomer thereof.

2. A pharmaceutical composition comprising a compound, stereoisomeric form, N-oxide, or pharmaceutically acceptable salt according to claim 1, and a pharmaceutically acceptable carrier, excipient or diluent.

\* \* \* \* \*